United States Patent
Gokhale

(10) Patent No.: US 11,191,460 B1
(45) Date of Patent: Dec. 7, 2021

(54) DEVICE AND METHOD FOR MEASURING BLOOD COMPONENTS

(71) Applicant: Shani Biotechnologies LLC, Austin, TX (US)

(72) Inventor: Sanjay Gokhale, Arlington, TX (US)

(73) Assignee: Shani Biotechnologies LLC, Austin, TX (US)

( * ) Notice: Subject to any disclaimer, the term of this patent is extended or adjusted under 35 U.S.C. 154(b) by 0 days.

(21) Appl. No.: 17/317,171

(22) Filed: May 11, 2021

Related U.S. Application Data

(60) Provisional application No. 63/052,115, filed on Jul. 15, 2020, provisional application No. 63/072,504, filed on Aug. 31, 2020.

(51) Int. Cl.
- *A61B 5/1455* (2006.01)
- *A61B 5/00* (2006.01)
- *A61B 5/103* (2006.01)

(52) U.S. Cl.
CPC ........ *A61B 5/14551* (2013.01); *A61B 5/1032* (2013.01); *A61B 5/443* (2013.01); *A61B 5/748* (2013.01); *A61B 5/7435* (2013.01)

(58) Field of Classification Search
CPC ...... A61B 5/1455–14558; A61B 5/1477–1482
See application file for complete search history.

(56) References Cited

U.S. PATENT DOCUMENTS

| | | | |
|---|---|---|---|
| 3,638,640 A | 2/1972 | Shaw | |
| 4,222,670 A | 9/1980 | Koshiishi | |
| 4,257,862 A | 3/1981 | Schnipelsky et al. | |
| 4,272,245 A | 6/1981 | Diamond et al. | |
| 4,397,725 A | 8/1983 | Enzer et al. | |
| 4,714,341 A | 12/1987 | Hamaguri et al. | |
| 4,723,554 A | 2/1988 | Oman et al. | |
| 5,041,187 A | 8/1991 | Hink et al. | |
| 5,111,817 A | 5/1992 | Clark et al. | |
| 5,242,832 A | 9/1993 | Sakata | |
| 5,277,181 A | 1/1994 | Mendelson et al. | |
| 5,377,674 A | 1/1995 | Kuestner | |
| 5,431,170 A | 7/1995 | Mathews | |
| 5,452,717 A | 9/1995 | Branigan et al. | |
| 5,575,285 A | 11/1996 | Takanashi et al. | |
| 5,692,503 A | 12/1997 | Kuenstner | |
| 5,720,284 A | 2/1998 | Aoyagi et al. | |

(Continued)

FOREIGN PATENT DOCUMENTS

AU 2002359193 B2 7/2003
AU 2004233870 B2 11/2004

(Continued)

OTHER PUBLICATIONS

Whitehead Jr. R.D. et al., "Methods and Analyzers for Hemoglobin Measurement in Clinical Laboratories and Field Settings", *Ann NY Acad Sci.* 1450(1):147-171 (Aug. 2019).

(Continued)

*Primary Examiner* — Meredith Weare
(74) *Attorney, Agent, or Firm* — Scully, Scott, Murphy & Presser, P.C.

(57) ABSTRACT

The present disclosure is directed to a method and device to determine the hemoglobin value of a mammal. The device includes a plurality of light emitting diodes, one or more sensors and a processor.

15 Claims, 13 Drawing Sheets

(56) References Cited

U.S. PATENT DOCUMENTS

| | | | |
|---|---|---|---|
| 5,800,349 | A | 9/1998 | Isaacson et al. |
| 5,830,132 | A * | 11/1998 | Robinson ............ A61B 5/1455 |
| | | | 600/310 |
| 5,842,979 | A | 12/1998 | Jarman |
| 5,879,294 | A | 3/1999 | Anderson et al. |
| 6,064,898 | A | 5/2000 | Aldrich |
| 6,104,938 | A | 8/2000 | Huiku et al. |
| 6,266,546 | B1 | 7/2001 | Steuer et al. |
| 6,305,804 | B1 | 10/2001 | Rice et al. |
| 6,554,788 | B1 | 4/2003 | Hunley et al. |
| 6,594,513 | B1 | 7/2003 | Jobsis et al. |
| 6,606,509 | B2 | 8/2003 | Schmitt |
| 6,622,095 | B2 | 9/2003 | Kobayashi et al. |
| 6,763,256 | B2 | 7/2004 | Kimball et al. |
| 6,802,812 | B1 | 10/2004 | Walker et al. |
| 6,819,949 | B2 | 11/2004 | Smith et al. |
| 6,831,733 | B2 | 12/2004 | Pettersson et al. |
| 6,927,843 | B2 | 8/2005 | Dick |
| 6,968,221 | B2 | 11/2005 | Rosenthal |
| 7,254,432 | B2 | 8/2007 | Fine |
| 7,288,759 | B2 | 10/2007 | Frangioni et al. |
| 7,379,167 | B2 | 5/2008 | Mawhirt et al. |
| 7,430,445 | B2 | 9/2008 | Esenaliev et al. |
| 7,523,649 | B2 | 4/2009 | Corey et al. |
| 7,551,950 | B2 | 6/2009 | Cheng |
| 7,608,042 | B2 | 10/2009 | Goldberger et al. |
| 7,782,447 | B2 | 8/2010 | Lindberg |
| 7,838,296 | B2 | 11/2010 | Corey et al. |
| 8,130,369 | B2 | 3/2012 | Barrett et al. |
| 8,175,610 | B2 | 5/2012 | Pi et al. |
| 8,175,670 | B2 | 5/2012 | Baker, Jr. et al. |
| 8,348,844 | B2 | 1/2013 | Kunjan et al. |
| 8,483,789 | B2 | 7/2013 | Higgins |
| 8,603,309 | B2 | 12/2013 | Cai et al. |
| 8,730,460 | B2 | 5/2014 | Yan et al. |
| 8,788,003 | B2 | 7/2014 | Schurman et al. |
| 9,037,207 | B2 | 5/2015 | Al-Ali et al. |
| D739,945 | S | 9/2015 | Cadio et al. |
| 9,161,364 | B2 | 10/2015 | Chen et al. |
| D778,445 | S | 2/2017 | Cadio et al. |
| 9,980,676 | B2 | 5/2018 | Newberry |
| 10,413,666 | B2 | 9/2019 | Al-Ali et al. |
| 10,444,232 | B2 | 10/2019 | Guo et al. |
| 2005/0267343 | A1 | 12/2005 | Woods et al. |
| 2005/0267346 | A1 | 12/2005 | Faber et al. |
| 2007/0106137 | A1 | 5/2007 | Baker, Jr. et al. |
| 2007/0129618 | A1 | 6/2007 | Goldberger et al. |
| 2007/0225675 | A1 | 9/2007 | Robinson et al. |
| 2011/0263031 | A1 | 10/2011 | Gomes et al. |
| 2015/0374276 | A1* | 12/2015 | Farkas ............... A61B 5/14558 |
| | | | 600/407 |
| 2016/0120449 | A1* | 5/2016 | Chiba .................. A61B 5/1459 |
| | | | 600/311 |
| 2017/0224271 | A1* | 8/2017 | Lachenbruch ......... A61B 5/746 |
| 2017/0303835 | A1* | 10/2017 | Bechtel ................ A61B 5/7221 |
| 2018/0011111 | A1 | 1/2018 | Keller et al. |
| 2019/0167161 | A1 | 6/2019 | Al-Ali et al. |
| 2020/0182778 | A1 | 6/2020 | Srivastava |
| 2021/0015365 | A1* | 1/2021 | Muehlemann ....... A61B 5/0073 |

FOREIGN PATENT DOCUMENTS

| | | |
|---|---|---|
| CA | 2 589 197 C | 3/2012 |
| CN | 1610827 A | 4/2005 |
| CN | 101490547 A | 7/2009 |
| CN | 104931441 A | 9/2015 |
| EP | 0 613 652 B1 | 9/1994 |
| EP | 1 620 002 B1 | 2/2006 |
| EP | 2 568 281 B1 | 3/2013 |
| IL | 124965 A1 | 8/2002 |
| JP | 2004-113353 A | 4/2004 |
| JP | 3817493 B2 | 9/2006 |
| JP | 4263247 B2 | 5/2009 |
| JP | 5645655 B2 | 12/2014 |
| JP | 6636410 B2 | 1/2020 |
| SE | 504 193 C2 | 12/1996 |
| SE | 530 244 C2 | 4/2008 |
| WO | 95/19134 A1 | 7/1995 |
| WO | 2011/013132 A1 | 2/2011 |

OTHER PUBLICATIONS

Vizbara V. et al., "Comparison of Green, Blue and Infrared Light in Wrist and Forehead Photoplethysmography", *Biomedical Engineering* pp. 78-81 (2013).

Yurdakök M., "Phototherapy in the Newborn: What's New?" *Journal of Pediatric and Neonatal Individualized Medicine* 4(2):e040255 (2015).

Zijlstra W.G. et al., "Absorption Spectra of Human Fetal and Adult Oxyhemoglobin, De-Oxyhemoglobin, Carboxyhemoglobin, and Methemoglobin", *Clinical Chemistry* 37(9):1633-1638 (1991).

https://www.sgs.com/en/news/2013/09/chemicals-in-medical-devices The EU regulation for the Registration, Evaluation, Authorization and Restriction of Chemicals (REACH) and the EU directive for the Reduction of Hazardous Substances (RoHS) are both soon to affect manufacturers of medical devices. (2013).

Masimo Corporation-FDA 501k Approval Accuracy pp. 1-21 (Feb. 27, 2020).

Letter to FDA by Members of US Senate https://www.warren.senate.gov/imo/media/doc/2020.01.25%20Letter%20to%20FDA%20re%20Bias%20in%20Pulse%20Oximetry%20Measurements.pdf (2021).

"The Joint Commission Continues to Study Overuse Issues", *The Joint Commission Perspectives* 32(5):4, May 8, 2012.

Absorption of Light by Organic Molecules https://archives.library.illinois.edu/erec/University%20Archives/1505050/Organic/Arenes/Chapter%205/sec5-14/5-14.htm (2021).

510(K) Summary NBM-2OOMP Pulse Oximetry Device 510(k) No. K124041, 12 pages Oct. 17, 2013.

Ash C. et al., "Effect of Wavelength and Beam Width on Penetration in Light-Tissue Interaction Using Computational Methods", Lasers Med Sci. 32(8):1909-1918 (2017).

Barker S.J. et al., "Continuous Noninvasive Hemoglobin Monitoring: A Measured Response to a Critical Review", Anesthesia Analg. 122(2):565-572 (Feb. 2016).

Bhutani V.K. et al., "Noninvasive Measurement of Total Serum Bilirubin in a Multiracial Predischarge Newborn Population to Assess the Risk of Severe Hyperbilirubinemia", Pediatrics 106(2):1-9 (Aug. 2000).

Bickler P.E. et al., "Effects of Skin Pigmentation on Pulse Oximeter Accuracy at Low Saturation", Anesthesiology 102(4):715-719 (Apr. 2005).

Bonadonna P., "Understanding Oxyhemoglobin", Monroe Community College (1 page) (2021).

Braverman I.M., "The Cutaneous Microcirculation", Journal of Investigave Dermatology Symposium Proceedings 5(1):3-9 (Dec. 2000).

Bruells C S et al., "Accuracy of the Masimo Pronto-7 System in Patients With Left Ventricular Assist Device", Journal of Cardiothoracic Surgery 8(159):1-6 (2013).

Chiamori N. et al., "Studies on the Determination of Bile Pigments-Spectrophotometric Determination of Bilirubin and Hemoglobin in Serum", Clinica Chimica Acta 6(1):1-6 (Jan. 1961).

Doshi R. et al., "Optical Sensor System for Hemoglobin Measurement", International Journal of Computational Engineering Research 3(7):41-45 (Jul. 2013).

Dutta S.S., "What is Oxygen Saturation?", https://www.news-medical.net/health/What-Is-Oxygen-Saturation.aspx (2021).

Evans I.V.R. et al., "Use of Oxyhemoglobin Saturation, Rather Than Oxygen Tension, as a Marker of Oxygenation in Cyanotic Patients", JAMA Pediatrics 171(10):1012-1014 (Oct. 2017).

Feiner J.R. et al., "Dark Skin Decreases the Accuracy of Pulse Oximeters at Low Oxygen Saturation: The Effects of Oximeter Probe Type and Gender", Anesth Analg 105(6):S18-S23 (Dec. 2007).

Felczak D., "Simulating Subsurface Scattering in Skin by Near-Infrared Light", Master's Thesis 2020.

(56) References Cited

OTHER PUBLICATIONS

Gajinov Z. et al., "Optical Properties of the Human Skin", Serbian Journal of Dermatology and Venereology 2(4):131-136 (2010).
Gayat E. et al., "Non-Invasive Measurement of Hemoglobin: Assessment of Two Different Point-of-Care Technologies", PLoS One 7(1):e30065 (2012).
Gush R.J. et al., "Discrimination of Capillary and Arterio-Venular Blood Flow in Skin by Laser Doppler Flowmetry", Medical & Biological Engineering & Computing 29:387-392 (Jul. 1991).
Hales J.R.S. et al., "Evidence for Skin Microvascular Compartmentalization by Laser-Doppler and Photoplethysmographic Techniques", Int J Microcirc Clin Exp 12:99-104 (Feb. 1993).
Hardesty J.H. et al., "Spectrophotometry and the Beer-Lambert Law: An Important Analytical Technique in Chemistry", Collin College Department of Chemistry pp. 1-6 (2010).
Jacques S.L., "Quick Analysis of Optical Spectra to Quantify Epidermal Melanin and Papillary Dermal Blood Content of Skin", Journal of Biophotonics 8(4):309-316 (2015).
Jansen K. et al., "Intravascular Photoacoustic Imaging: A New Tool for Vulnerable Plaque Identification", Ultrasound in Med & Biol 40(6):1037-1048 (2014).
Kim S-H et al., "Accuracy of Continuous Noninvasive Hemoglobin Monitoring: A Systematic Review and Meta-Analysis", Anesth Analg 119(2):332-346 (Aug. 2014).
Kongshoj B. et al., "Pheomelanin and Eumelanin in Human Skin Determined by High-Performance Liquid Chromatography and its Relation to In Vivo Reflectance Measurements", Photodermatol Photoimmunol Photomed 22(3):141-147 (Jun. 2006).
Krishnaswamy A. et al., A Study on Skin Optics-Natural Phenomena Simulation Group, School of Computer Science, University of Waterloo, Canada, Technical Report CS-2004-01 (Jan. 2004).
Kollias N., "The Spectroscopy of Human Melanin Pigmentation", pp. 31-38 (1995).
Lederman S., "Molecular Spectra and The Raman Effect—A Short Review", Contract No. DAHCO4-69-C-0077, ARPA Order No. 1442, Amendment No. 2, Program Code No. 9E30, Polytechnic Institute of Brooklyn Department of Aerospace Engineering and Applied Mechanics (Jun. 1971).
Lister T. et al., "Optical Properties of Human Skin", Journal of Biomedical Optics 17(9):090901-1 (Sep. 2012).
Liu P. et al., "Specific Absorption Spectra of Hemoglobin at Different PO2 Levels: Potential Noninvasive Method to Detect PO2 in Tissues", Journal of Biomedical Optics 17(12):125002 (Dec. 2012).
Manning T.O. et al., "Cutaneous Laser-Doppler Velocimetry in Nine Animal Species", American Journal of Veterinary Research 52(12):1960-1964 (Dec. 1991).
Matts P.J. et al., "The Distribution of Melanin in Skin Determined In Vivo", British Journal of Dermatology 156:620-628 (2007).
McEwen M. et al., "Noninvasive Detection of Bilirubin Using Pulsatile Absorption", Australas Phys Eng Sci Med. 29(1):78-83 (2006).
Mignon C. et al., "Shedding Light on the Variability of Optical Skin Properties: Finding a Path Towards More Accurate Prediction of Light Propagation in Human Cutaneous Compartments", Biomedical Optics Express 9(2):852-872 (Feb. 1, 2018).
Monteiro-Riviere N.A. et al., "Interspecies and Interregional Analysis of the Comparative Histologic Thickness and Laser Doppler Blood Flow Measurements at Five Cutaneous Sites in Nine Species", J. Invest Dermatol 95(5):582-586 (Nov. 1990).
Murray A.K. et al., "Comparison of Red and Green Laser Doppler Imaging of Blood Flow", Lasers in Surgery and Medicine 35:191-200 (2004).
Nagar G. et al., "Effect of Phototherapy on the Diagnostic Accuracy of Transcutaneous Bilirubin in Preterm Infants", Journal of Clinical Neonatology 6(3):148-153 (Jul.-Sep. 2017).
Otto J M et al., "Haemoglobin Concentration and Mass as Determinants of Exercise Performance and of Surgical Outcome", Extreme Physiology & Medicine 2(33):1-8 (2013).
Petzelbauer P. et al., "Chapter 9 Cutaneous Vasculature", Fitzpatrick's Dermatology, 9th Edition McGraw Hill USA (2019), https://accessmedicine.mhmedical.com/content.aspx?bookid=2570&sectionid=210415779.
Randeberg L.L. et al., "In Vivo Spectroscopy of Jaundiced Newborn Skin Reveals More than a Bilirubin Index", Acta Paediatrica 94(1):65-71 (2005).
Robles F.E. et al., "Assessing Hemoglobin Concentration Using Spectroscopic Optical Coherence Tomography for Feasibility of Tissue Diagnostics", Biomedical Optics Express 1(1):310-317 (Aug. 2, 2010).
Saidi I.S. et al., "Preliminary Clinical Results of a Transcutaneous Reflectance Spectrophotometer for the Detection of Bilirubin in Neonates", Conference on Lasers and Electro-Optics, CTuS3 (1991).
Saka M. et al., "Linear Superposition of Sensory-Evoked and Ongoing Cortical Hemodynamics", Fronteirs in Neuroenergetics 2(23):1-13 (Aug. 2010).
Sandby-Moller J. et al., "Epidermal Thickness at Different Body Sites: Relationship to Age, Gender, Pigmentation, Blood Content, Skin Type and Smoking", Acta Derm Venereol 83:410-413 (2003).
Sankaran V.G. et al., "The Switch from Fetal to Adult Hemoglobin", Cold Spring Harbor Perspect Med. 3(1):a011643 (Jan. 2013).
Sekar S K V et al., "Diffuse Optical Characterization of Collagen Absorption from 500 to 1700 nm", Journal of Biomedical Optics 22(1):015006 (Jan. 2017).
Seo Y J et al., "Lowest Oxyhemoglobin Saturation May Be an Independent Factor Influencing Auditory Function in Severe Obstructive Sleep Apnea", Journal of Clinical Sleep Medicine 12(5):653-658 (2016).
Siu LY et al., "Evaluation of a Transcutaneous Bilirubinometer with Two Optical Paths in Chinese Preterm Infants", HK J Paediatr (New Series) 15:132-140 (2010).
Tanghetti E. et al., "A Comparative Study With a 755 nm Picosecond Alexandrite Laser With a Diffractive Lens Array and a 532 nm/1,064 nm Nd:YAG With a Holographic Optic", Lasers in Surgery and Medicine 50:37-44 (2018).
Treesirichod A. et al., "Correlation Between Skin Color Evaluation by Skin Color Scale Chart and Narrowband Reflectance Spectrophotometer", Indian Journal of Dermatology 59(4):339-342 (Jul.-Aug. 2014).
Tseng S-H et al., "Chromophore Concentrations, Absorption and Scattering Properties of Human Skin In-Vivo", Opt Express 17(17):14599-14617 (Aug. 17, 2009).
Ubbink D.T. et al., "Can the Green Laser Doppler Measure Skin-Nutritive Perfusion in Patients With Peripheral Vascular Disease?", Journal of Vascular Research 37(3):195-201 (Jun. 2000).
Ward W.H. et al., "Clinical Presentation and Staging of Melanoma-Cutaneous Melanoma", Etiology and Therapy (Dec. 2017).
Oxyhemoglobin, Arterial (Blood Gas), Test ID LAB5308, UNC Medical Center (1 page) (2021), https:www.uncmedicalcenter.org/mclendon-clinical-laboratories/available-tests/oxyhemoglobin-arterial-blood-gas.

* cited by examiner

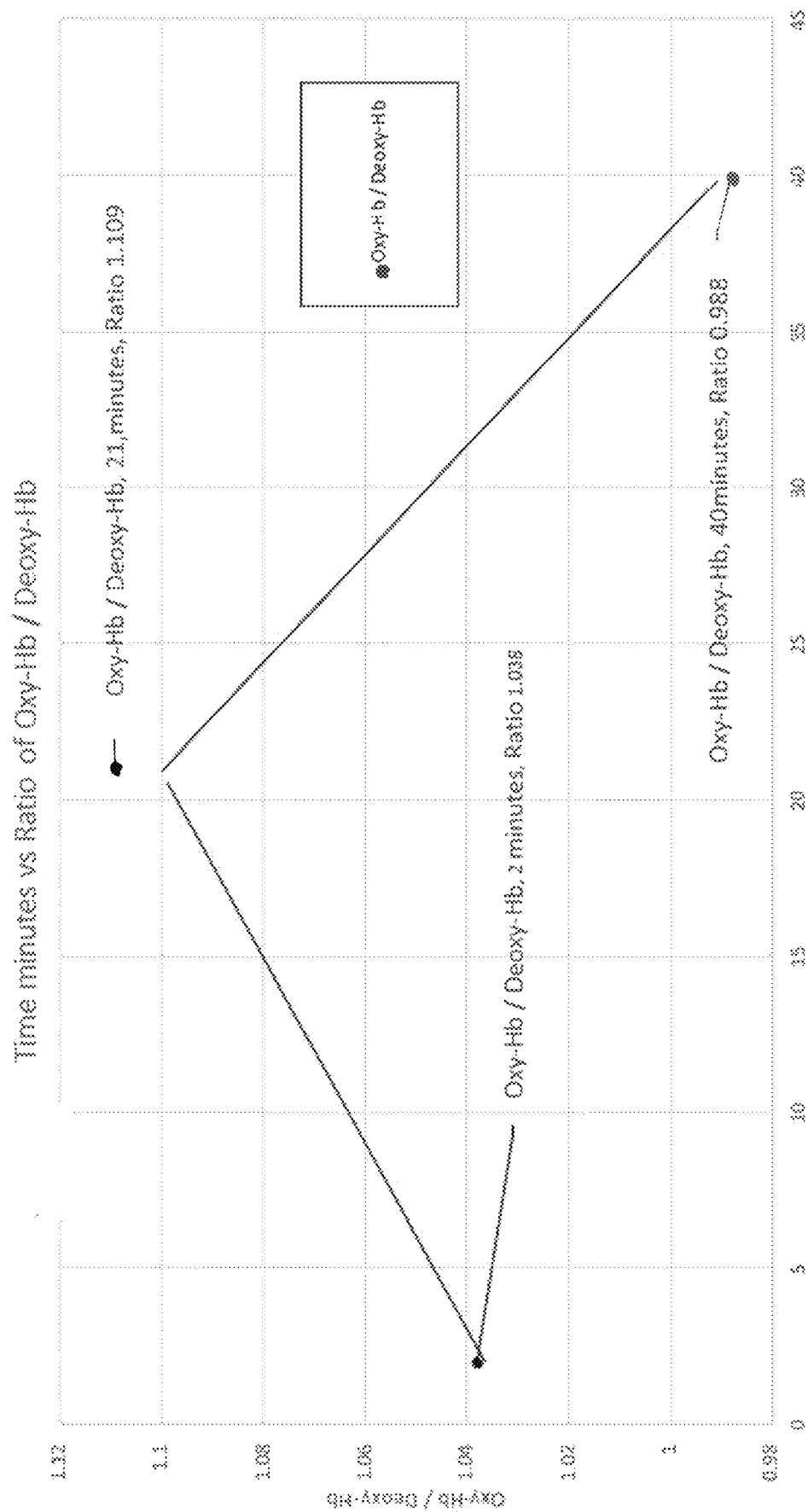

DEVICE AND METHOD FOR MEASURING BLOOD COMPONENTS

CROSS REFERENCE TO RELATED APPLICATION

This application claims the benefit of both of U.S. Provisional Patent Application Ser. No. 63/052,115 filed on Jul. 15, 2020 and U.S. Provisional Patent Application Ser. No. 63/072,504 filed on Aug. 31, 2020, the entire contents of each of which are herein incorporated by reference.

BACKGROUND OF THE DISCLOSURE

The measurement and monitoring of blood constituents such as hemoglobin (Hb) and its species such as oxyhemoglobin (O-Hb) is often an invasive procedure. The blood draw can cause discomfort to the patient and increases the risk of infection. The adverse effects of constant and often difficult blood draws on newborns and infants are even more pronounced. Frequent and constant hemoglobin measurements are clinically indicated in a wide variety of conditions such as (but not limited to) anemia, emergency and critical care including patients infected with Coronavirus Disease of 2019 (COVID-19), hemoglobinopathies such as sickle cell disease (hemoglobin-S), hematological malignancies, and peri-operative management after major surgeries such as spine surgery etc. In addition, these parameters are part of routine health maintenance in healthy subjects and are increasingly being used to monitor athletic performance.

Thus, frequent measurements of Hb and O-Hb have wide applications in healthy adults and children, athletes, patients recovering from various illnesses, as well as patients admitted in the hospital setting. Although the available invasive techniques are established, they require the presence of medical personnel and laboratory equipment. Typical laboratory methods include the cyanmethemoglobin (CM) method, the copper sulfate technique (CST), the automated hematology analyzers (AHA) and the color based analytical devices. These requirements drive up the cost, as well as the amount of time for the results to be available for the clinical use. There are a few 'point of care (POC)' hemoglobin tests such as the HemoCue which can be done in the field or potentially at the bedside. However, it still requires obtaining a blood sample from the patient.

There are non-invasive methods, however they suffer from variability and limitations during low perfusion states such as shock, as well as inability to measure hemoglobin values across a broad range.

What is desired is a non-invasive system, devices, and method to measure various blood components. Embodiments of the present disclosure provide devices and methods that address the above needs.

SUMMARY OF THE DISCLOSURE

The present disclosure is directed to the measurement of hemoglobin concentration using reflectance spectroscopy. The advantages of this technology are a simple, portable, and easy to use hand-held device (as described below) to measure the hemoglobin (Hb) concentration in real time, and a method for continuous (or nearly continuous) non-invasive Hb monitoring. This method also offers an advantage of measuring the ratio of oxy-hemoglobin (O-Hb) concentration to the deoxy-hemoglobin (d-Hb) concentration.

BRIEF DESCRIPTION OF THE DRAWINGS

The present disclosure will be better understood by reference to the following drawings, which are provided as illustrative of certain embodiments of the subject application, and not meant to limit the scope of the present disclosure.

FIG. 13 is a graph of E1 to E2 ratio over time.

DETAILED DESCRIPTION OF THE DISCLOSURE

Figure 1:
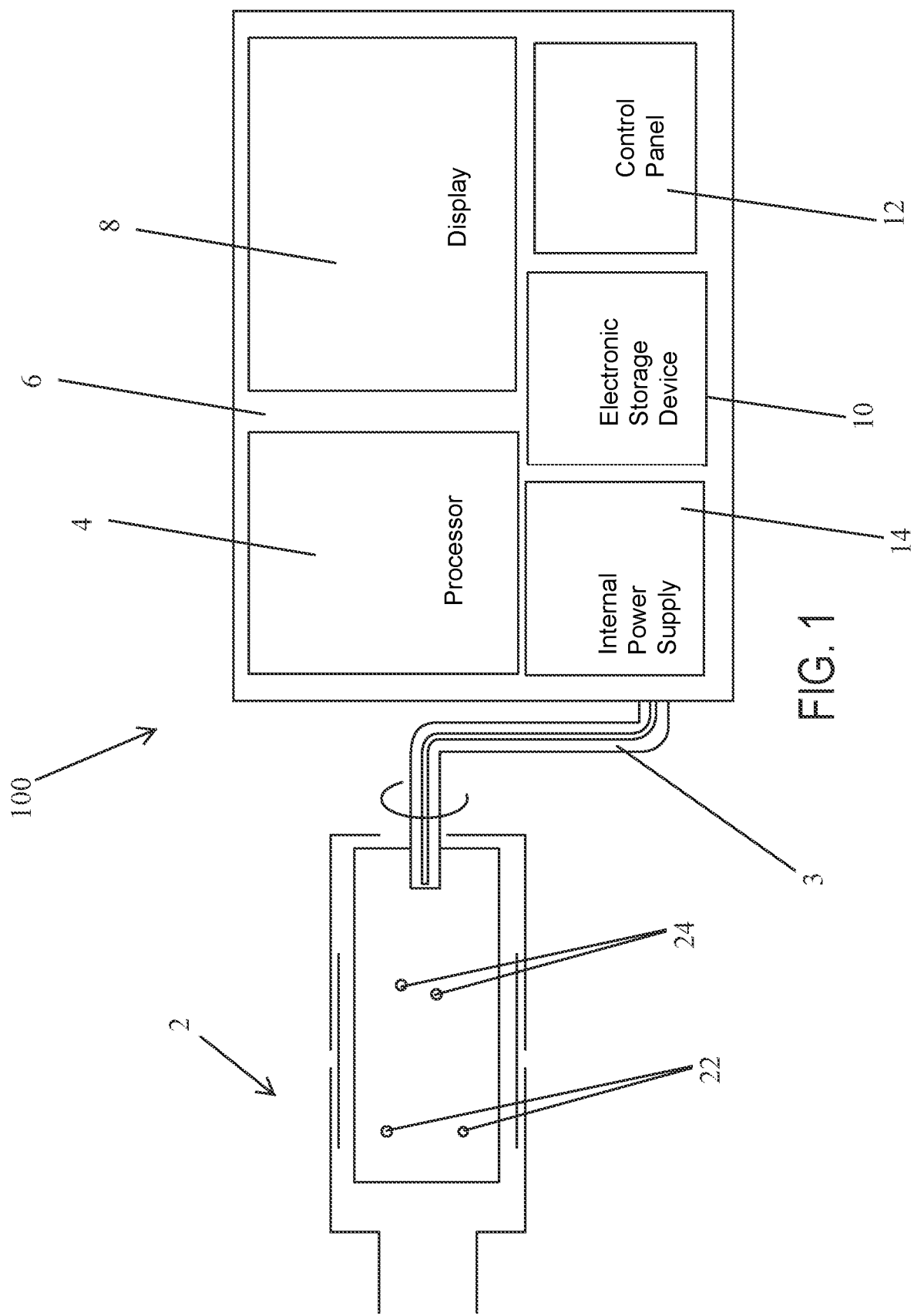
FIG. 1 is a graphical illustration of a device of the present disclosure.

In the discussion and claims herein, the term "about" indicates that the value listed may be somewhat altered, as long as the alteration does not result in nonconformance of the process or device. For example, for some elements the term "about" can refer to a variation of ±0.1%, for other elements, the term "about" can refer to a variation of ±1% or ±10%, or any point therein.

As used herein, the term "substantially", or "substantial", is a broad term and is used in its ordinary sense, including, without limitation, being largely but not necessarily wholly that which is specified, which is equally applicable when used in a negative connotation to refer to the complete or near complete lack of an action, characteristic, property, state, structure, item, or result. For example, a surface that is "substantially" flat would mean either completely flat, or so nearly flat that the effect would be the same as if it were completely flat.

As used herein terms such as "a", "an" and "the" are not intended to refer to only a singular entity but include the general class of which a specific example may be used for illustration.

As used herein, terms defined in the singular are intended to include those terms defined in the plural and vice versa.

References in the specification to "one embodiment", "certain embodiments", some embodiments" or "an embodiment", indicate that the embodiment(s) described may include a particular feature or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper", "lower", "right", "left", "vertical", "horizontal", "top", "bottom", and derivatives thereof shall relate to the invention, as it is oriented in the drawing figures. The terms "overlying", "atop", "positioned on" or "positioned atop" means that a first element, is present on a second element, wherein intervening elements interface between the first element and the second element. The term "direct contact" or "attached to" means that a first element and a second element are connected without any intermediary element at the interface of the two elements.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc.

The present disclosure is directed to devices and methods of measuring various blood components, such as different forms of hemoglobin, such as oxy-hemoglobin (O-Hb) and deoxy-hemoglobin (d-Hb).

A hemoglobin molecule has two units, Heme and Globin. The Heme part has one iron as $Fe^{+2}$ or Ferrous form and Pyrrole rings. Globin is tetrameric or with four amino acid chains. These chains are Alpha, Beta, Gamma and Delta globin chains. Hemoglobin therefore has a Heme and Four Globin Chains. For example, Hb-A has two alpha and two beta chains. Table 1 below summarizes the three types of Hemoglobins in health.

TABLE 1

| Hemoglobin-A | Heme+ α2β2 | Hb-A | 98 to 98.5% of total hemoglobin |
|---|---|---|---|
| Hemoglobin-A2 | Heme+ α2δ2 | Hb-A2 | 1 to 1.5% of total hemoglobin |
| Hemoglobin-F | Heme+ α2γ2 | Hb-F | In Newborns till around 8 months |

Oxy-hemoglobin refers to the amount of hemoglobin having oxygen bound to the heme component, while deoxy-hemoglobin refers to the amount of hemoglobin not having bound oxygen. Oxy-hemoglobin and total hemoglobin retain a ratio based on health. When hemoglobin is broken down, globin chains are added to the amino acid pool. Heme is split and all the Pyrrole rings open. These are later metabolized into Bilirubin. When the concentrations are high, more light is being absorbed. Hence, by measuring reflected light, as discussed further below, the concentration of oxy-hemoglobin, and deoxy-hemoglobin can be determined.

Based on the above a probe device can be utilized to measure reflected light to determine a ratio of oxy-hemoglobin to deoxy-hemoglobin. For example, a probe device 100 is shown in FIG. 1. Oxy-hemoglobin (O-Hb) and deoxy-hemoglobin (d-Hb) have unique spectroscopic properties as compared to each other. O-Hb has an absorption peak between about 515 nm to about 535 nm, between about 520 nm to about 530 nm, or about 525 nm. d-Hb has an absorption peak at between about 540 nm to about 560 nm, between about 545 nm to about 555 nm, or about 550 nm.

The device 100 can include a probe (device) 2 and a processor 4. As used herein, the term "processor" may refer to, is part of, or includes circuitry capable of sequentially and automatically carrying out a sequence of arithmetic or logical operations; recording, storing, and/or transferring digital data. The term "processor" may refer to one or more application processors, one or more baseband processors, a physical central processing unit (CPU), a single or multiple-core processor, and/or any other device capable of executing or otherwise operating computer-executable instructions, such as program code, software modules, and/or functional processes.

In this embodiment the probe 2 is connected to the processor 4 through a suitable cable 3, which is configured to transmit electrical signals. However, in other embodiments, the probe 2 can wirelessly communicate with the processor 4 through any suitable wireless protocol, including but not limited to Wi-Fi, Bluetooth®, Near Field Communication (NFC), etc. In yet other embodiments, the processor 4 can be within the probe 2 itself.

The processor 4 can be included in a housing 6. The housing 6 can also include an electronic storage device 10. As used herein, the term "electronic storage device" includes any type of integrated circuit, microcontroller and/or other storage device adapted for storing digital data including, without limitation, ROM, PROM, EEPROM, DRAM, SDRAM, DDR/2 SDRAM, EDO/FPMS, RLDRAM, SRAM, "flash" memory (e.g., NAND/NOR), 3D memory, and PSRAM.

The housing 6 can also include a display 8. The display 8 can be any suitable display, such as a liquid crystal display (LCD), a cathode ray tube display, a light emitting diode (LED) display, or the like, which can display various information determined by the probe 2 and/or stored within the memory 10. Optionally, the display 8 can also be an input by receiving touch input from a user on or near a portion of the display 8. Alternatively, or in addition to, the display 8 being an input, the housing 6 can also include a control panel 12, which can accept various inputs from a user. These inputs are described in more detail below.

Optionally, in this embodiment, the housing 6 can also include an internal power supply 14, such as a battery. However, in other embodiments, the probe 2 and/or processor 4 can receive power from an external source. In yet other embodiments, the probe 2 itself can include a power supply 14.

Figure 2:
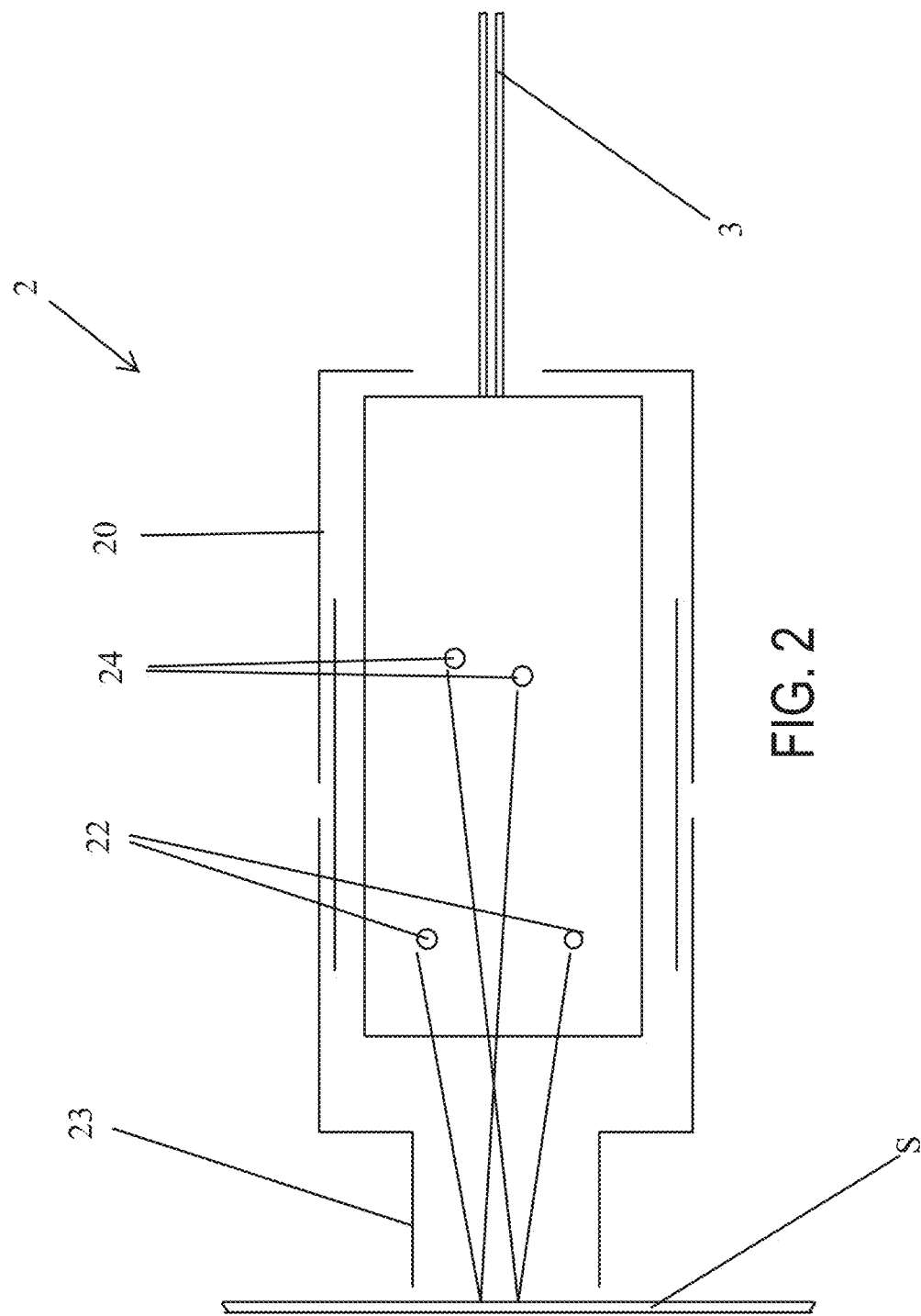
FIG. 2 is a graphical illustration of a probe of the device of the present disclosure.

The probe 2 is illustrated in more detail in FIG. 2, including a nozzle 23 of the probe 2. The nozzle 23 can be any suitable, hollow, or tubular structure that can be formed to be any suitable length to allow for accurate measurement of reflected light by the probe 2.

In FIG. 2, within the probe housing 20 are a plurality of light emitting diodes 22. The wavelengths of each of the plurality of these light emitting diodes 22 can be the same or different, can be fixed or variable, and can be any suitable wavelength, in any suitable range, such as about 450 nm to about 580 nm. Specific examples of such wavelengths include, but are not limited to about 525 nm, about, 545 nm, about 550 nm, and about 575 nm. However, in other embodiments, the wavelengths can differ from any of the above values by about 0.001%, about 0.01%, about 0.1%, about 0.5%, about 1%, about 2%, about 3%, about 4%, about 5%, about 7%, about 9%, about 10%, about 13%, about 15%, about 20% or more.

The plurality of light emitting diodes 22 can be activated individually, or in any suitable sequence, to illuminate a surface, such as a skin surface (any suitable portion of the epidermis) of a mammal.

Upon illumination from the light emitting diodes 22, one or more sensors 24 (two are shown in the figures for illustrative purposes), which are configured to sense an amount of light, for example a photodiode, do measure the light reflected from the surface. These one or more sensors 24 then convert that measured light to a suitable electrical signal. In the present disclosure, the light emitting diodes 22 can emit light at any given interval, from about 0.1 second or less, to about 0.5 seconds or more, about 1 second or more, about 5 seconds or more, about 30 seconds or more, about 1 minute or more, about 2 minutes or more, about 5 minutes or more, or about 10 minutes or more. Accordingly, the one or more sensors 24 can be configured to sense the amount of reflected light at times corresponding to whatever time period is selected for light emission.

Figure 3:
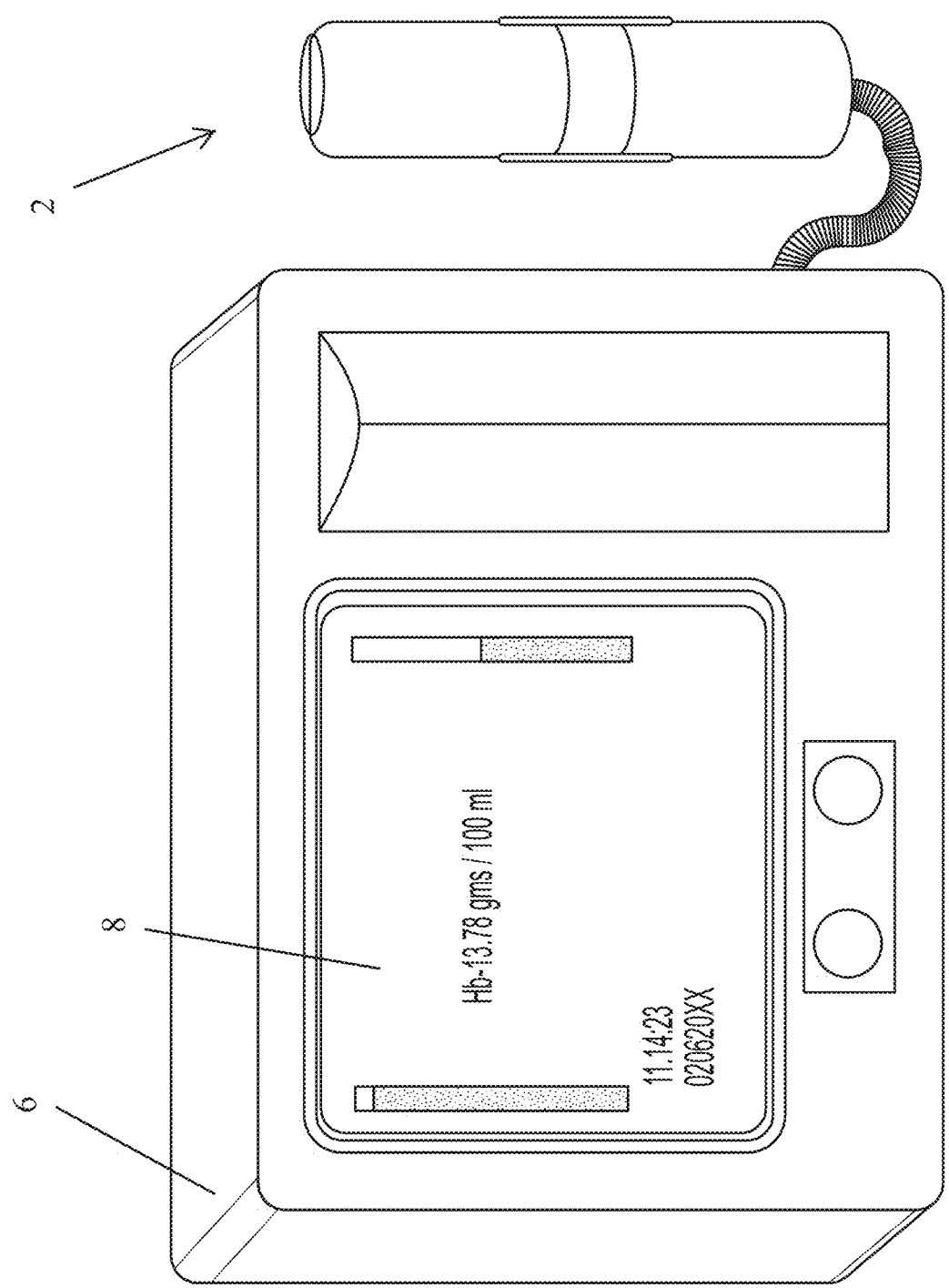
FIG. 3 is a graphical illustration of a probe of the device and a housing of the present disclosure.

FIG. 3 is one embodiment of a probe 2 connected to a housing 6, with the housing 6 including the display 8 and various inputs and controls. The opening at the vertical upper portion of the probe 2 is where each light is transmitted (from the plurality of light emitting diodes 22) and collected (by the one or more sensors 24) through. This opening can be a void, or can include a substantially transparent barrier, such as a plastic and/or glass barrier.

The display 8, which can optionally be used as an input, can be used to display various data, such as the name of the mammal the probe 2 is to be applied to, date, time, status of the probe 2, power indicator, total hemoglobin, oxy-hemoglobin level, deoxy-hemoglobin level, and/or a ratio of oxy-hemoglobin to deoxy-hemoglobin.

Figure 4:
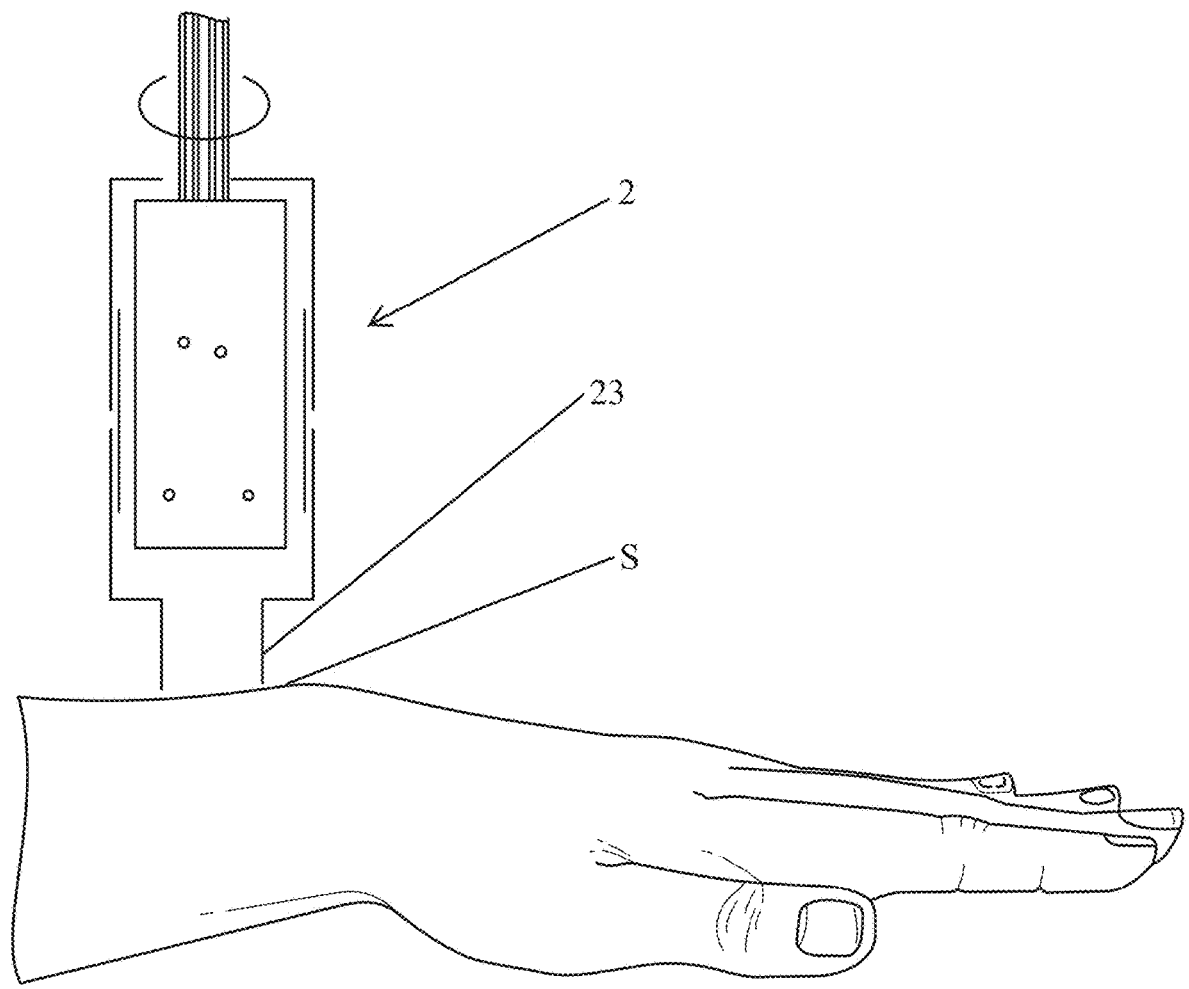
FIG. 4 is a graphical illustration of a probe near a human mammal's skin surface.

The probe 2 can be placed into contact with any portion of a mammal's skin (S), for example a human's wrist and/or hand as shown in FIG. 4. As can be seen in FIG. 4, the nozzle 23 of the probe 2 is placed near or in contact with the portion of the human's wrist and is held there by another user (or the human themselves, or by a wearable structure).

Figure 5:
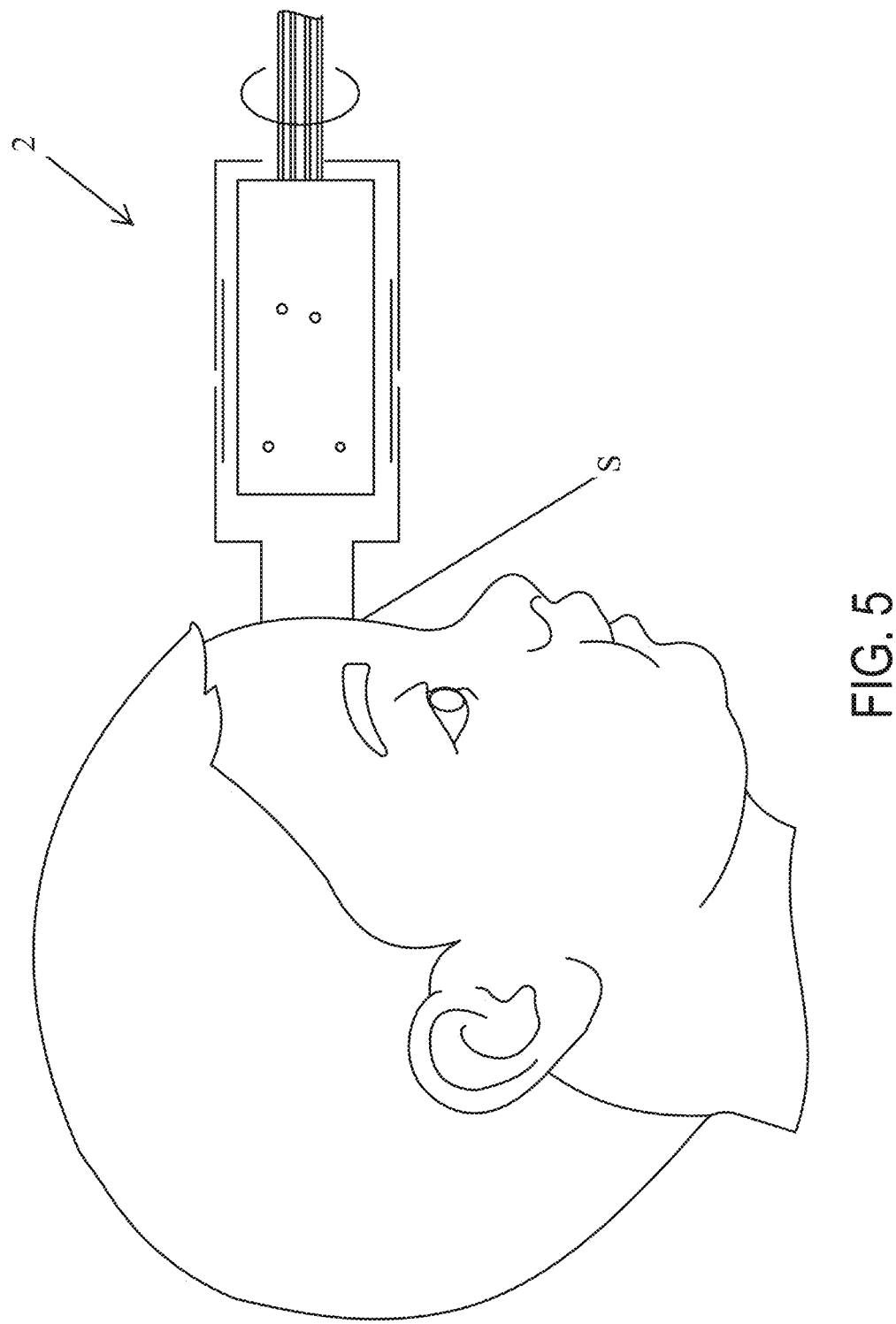
FIG. 5 is a graphical illustration of a probe near a human mammal's skin surface.

In another embodiment, the probe can be placed into contact with a human's forehead, as seen in FIG. 5.

Alternatively, to the probe of FIGS. 4 and 5, the light emitting diodes 22 and one or more sensors 24 can be included in a wearable structure, for example, similarly to a watch. This wearable structure can also include the processor 4, or the wearable structure can be configured to transmit data to the processor 4 that is external to the wearable structure.

Regardless of probe 2 structure, during operation of the disclosed device in determining oxy-hemoglobin level, deoxy-hemoglobin level, and/or a ratio of oxy-hemoglobin to deoxy-hemoglobin, the light of the plurality of light emitting diodes 22 is directed towards a portion of the mammal's skin.

If that mammal has a relatively low hemoglobin level, a greater proportion of the light emitted from the light emitting diodes 22 is reflected back and received by the one or more sensors 24. For example, more light emitted from the light emitting diodes 22 passes through the epidermis and reflects off of both the upper vascular plexus and the lower vascular plexus, and then back again through the epidermis. Thus, in this example, less light is absorbed in the dermal papillae between the lower vascular plexus and the upper vascular plexus, and between the upper vascular plexus and the epidermis.

In contrast, if that mammal has a relatively high hemoglobin level, a lesser proportion of the light emitted from the light emitting diodes 22 is reflected back and received by the one or more sensors 24. For example, less light emitted from the light emitting diodes 22 passes through the epidermis and reflects off of both the upper vascular plexus or lower vascular plexus, and then back again through the epidermis. Thus, in this example, more light is absorbed in the dermal papillae between the lower vascular plexus and the upper vascular plexus, and between the upper vascular plexus and the epidermis.

The relationship between the reflection of light and hemoglobin levels is discussed below in reference to FIGS. 6 and 7.

Figure 6:
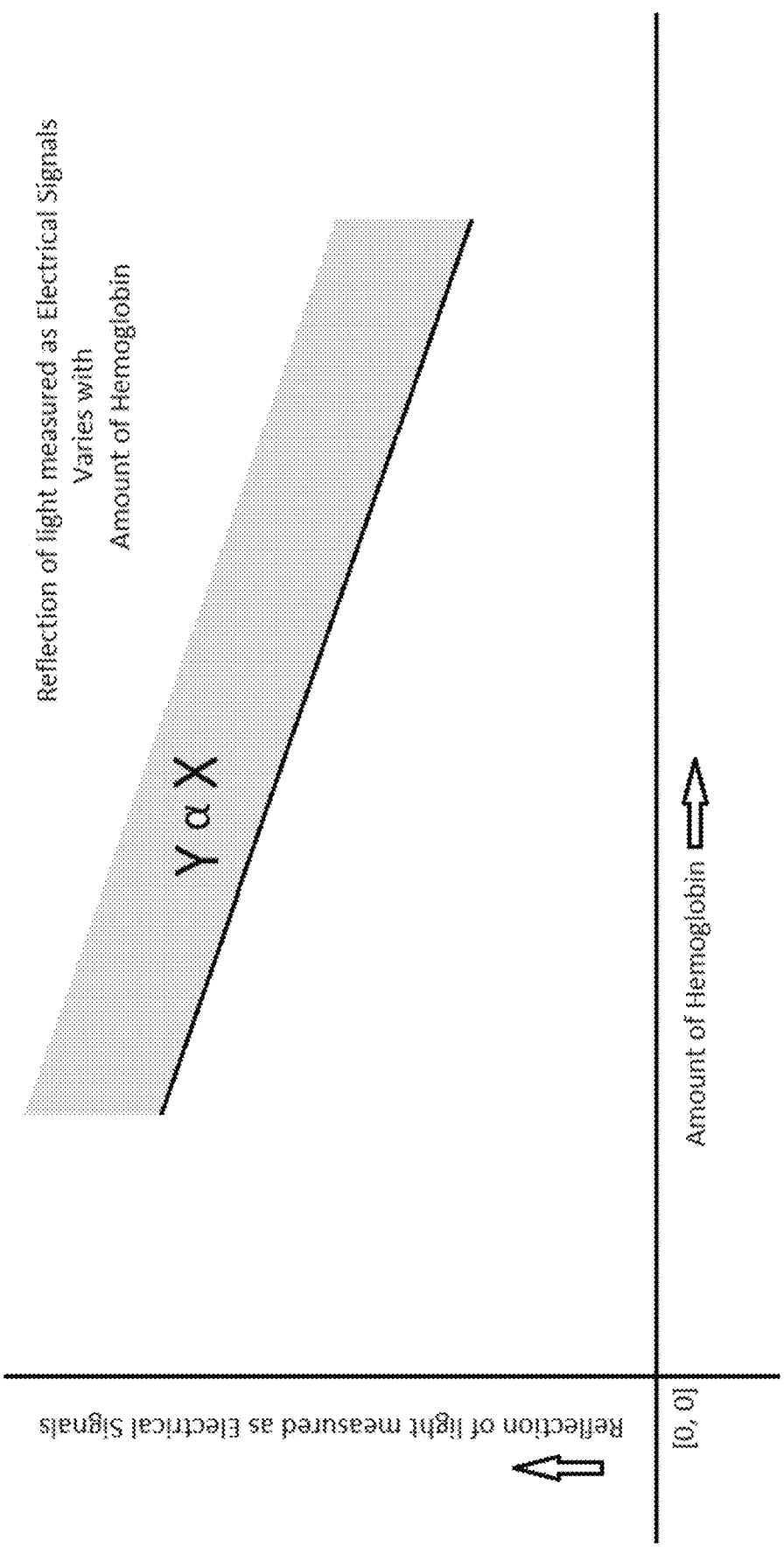
FIG. 6 is a graph of the reflection of light level as compared to hemoglobin level.
Figure 7:
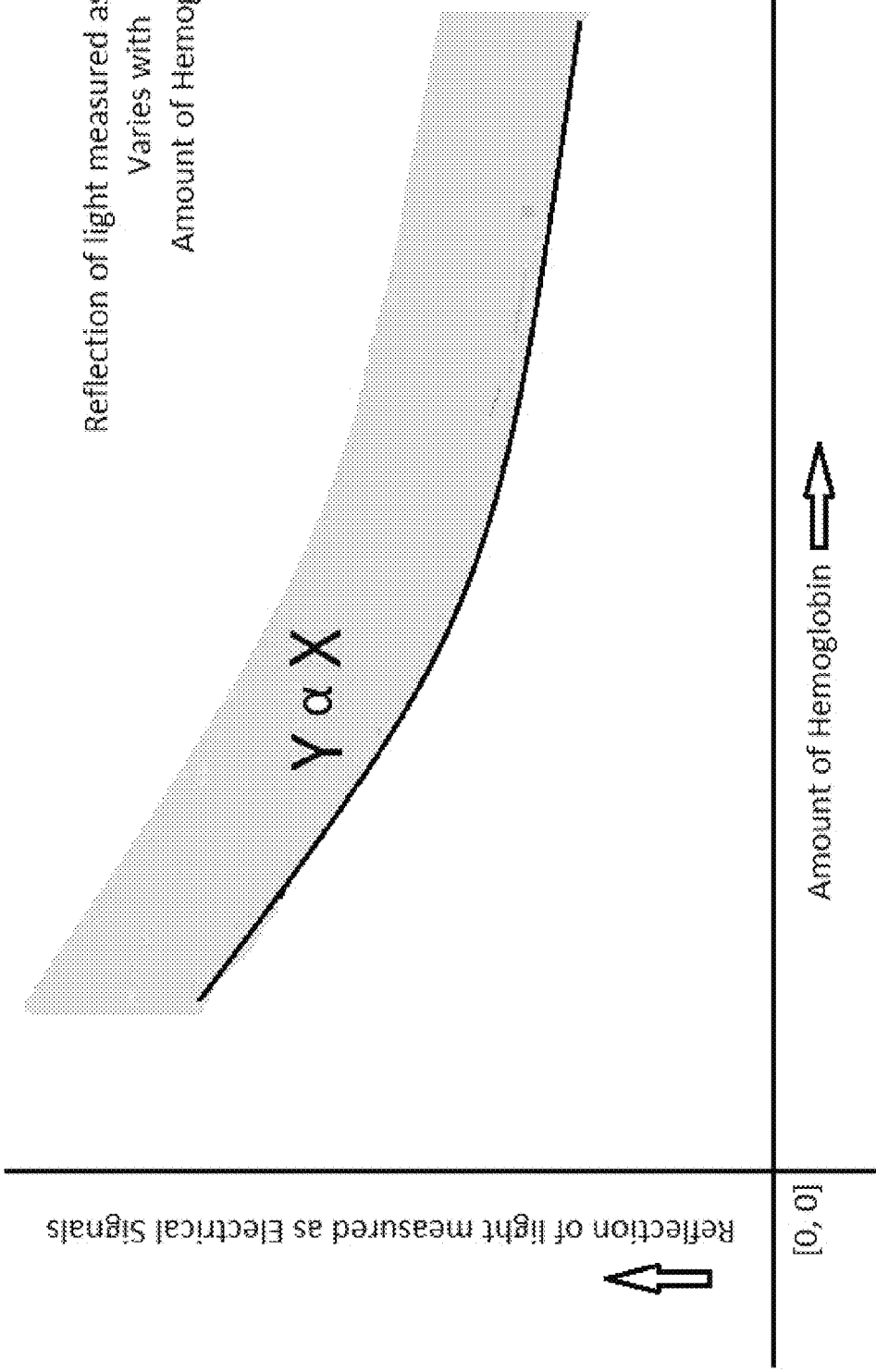
FIG. 7 is a graph of the reflection of light level as compared to hemoglobin level.

The relationship between the amount of reflection of light measured as an electrical signal (current) (on the Y-axis) and amount of hemoglobin in the blood (on the X-axis) is shown in FIGS. 6 and 7. These graphs are based on several readings from mammals, humans specifically, with different skin color. Mammals with a lighter skin have less melanin in their skin, as compared to mammals with darker skin. In FIG. 6 skin color is kept constant, so that the relationship between electrical signal and the hemoglobin concentration is linear.

Specifically in FIG. 6, the graph illustrates the relationship between the amount of reflection of light measured as an electrical signal (current) (on the Y-axis) by the one or more sensors 24 and amount of hemoglobin in the blood (on the X-axis) of the mammal. The relationship is substantially linear as indicated by the straight line, which applies under the assumption that melanin concentration in the skin of the mammal (or the skin of a plurality of mammals) is substantially constant. The grey shaded area above the substantially straight line represents the symmetrical vertical shift in this linear relationship depending on the skin melanin concentration.

In partial contrast to FIG. 6, as seen in FIG. 7 a graph illustrates the relationship between the amount of reflection of light measured as an electrical signal (current) (on the Y-axis) by the one or more sensors 24 and amount of hemoglobin in the blood (on the X-axis) of the mammal. The line in FIG. 7 is substantially logarithmic due the varying melanin levels of the skin of the humans measured to arrive at the data. The grey shaded area above represents the vertical shift in this relationship depending on the variability in the skin melanin concentration of the mammal under measurement.

The difference between FIG. 6 and FIG. 7 demonstrates the impact melanin content of the mammal's skin can have on the accuracy of a hemoglobin reading.

As a further demonstration of the effect melanin has on hemoglobin determinations, data is presented and discussed with reference to FIGS. 7-10.

Figure 8:
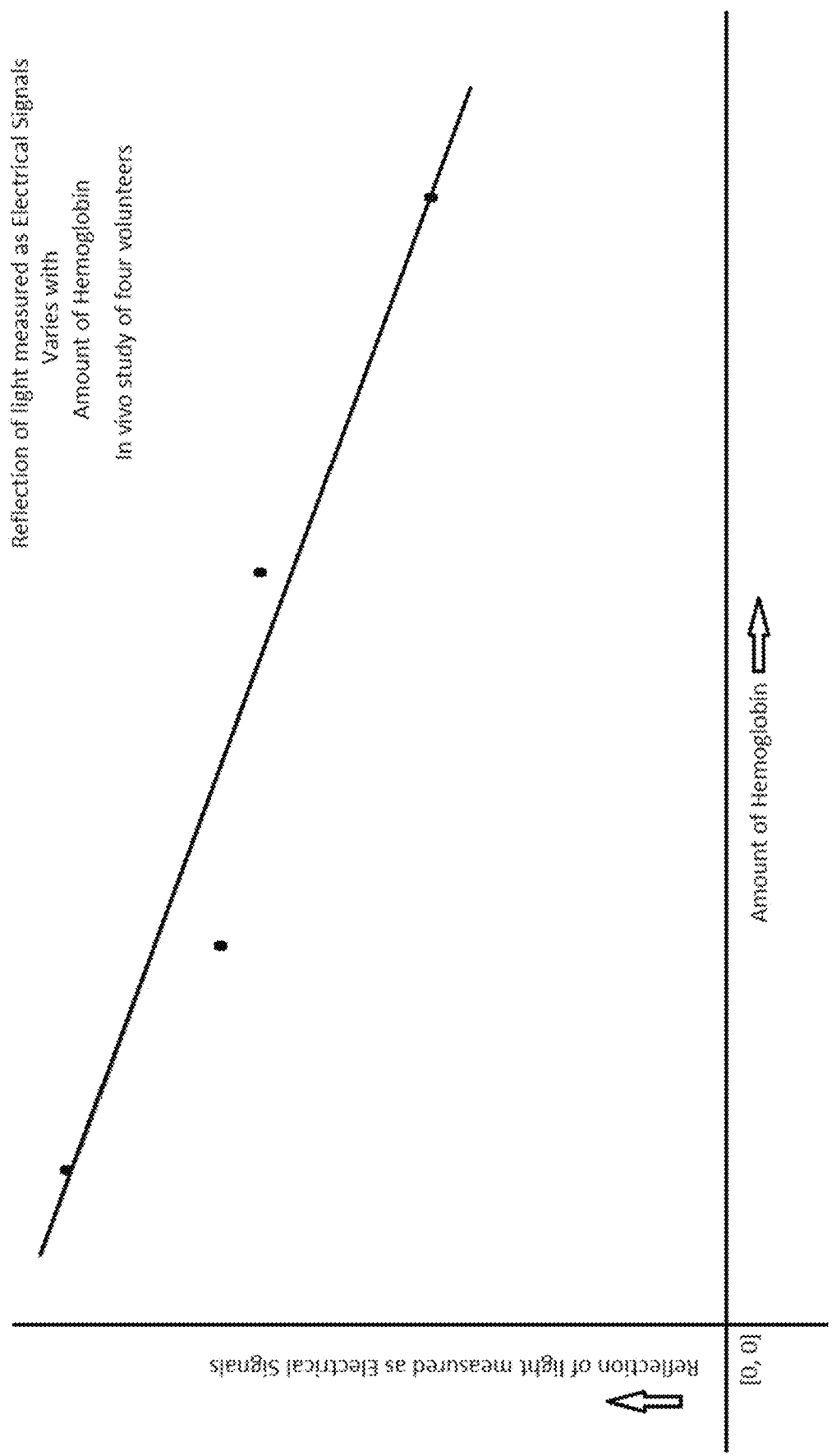
FIG. 8 is a graph of the reflection of light level as compared to hemoglobin level.

FIG. 8 is the graphical representation of data from four different individuals, with similar melanin content (as measured on the Felix Von Luschan (VLS) skin color chart), using the probe 2 on the same site in each individual (back of the wrist). The VLS scale provides a correlation of the color grade of a human's skin (from 1-36) to the estimated melanin content of that human's skin. Thus, the VLS scale can be relied upon to provide a melanin content substantially accurately for a human based on their assignment to one of 36 skin colors.

Referring again to FIG. 8, the amount of reflection of light measured as an electrical signal (current) is plotted on the Y-axis, measured by the one or more sensors 24, and amount of hemoglobin (measured using the conventional blood draw method) in the blood of the individual is plotted on the X-axis. The relationship is substantially linear as shown with the substantially straight line. As a comparison, the blood hemoglobin of the four different individuals was also measured using the standard cyanmethemoglobin laboratory technique, as shown by the four data points in FIG. 8. As can be seen, there is a substantially accurate correlation between measured light values translated to hemoglobin content as compared to blood tested hemoglobin levels.

As one way to correct for the influence varying melanin levels has on optical hemoglobin determinations, the probe 2 could be made so that the nozzle 23 has a relatively small opening size. Under this embodiment, the melanin concentration of the subject's skin is finite and defined, and if the same amount of light is passed from the plurality of LEDs 22 to a smaller skin surface are of the mammal, the emitted light will encounter a relatively smaller amount of melanin. Since the concentration of melanin is typically in the microgram range, and the concentration of hemoglobin is typically in the gram range, the impact of varying melanin concentrations on optical hemoglobin determinations can be minimized.

As another way to correct for the influence varying melanin levels has on optical hemoglobin determinations, melanin levels can be considered, as discussed below.

Figure 9:
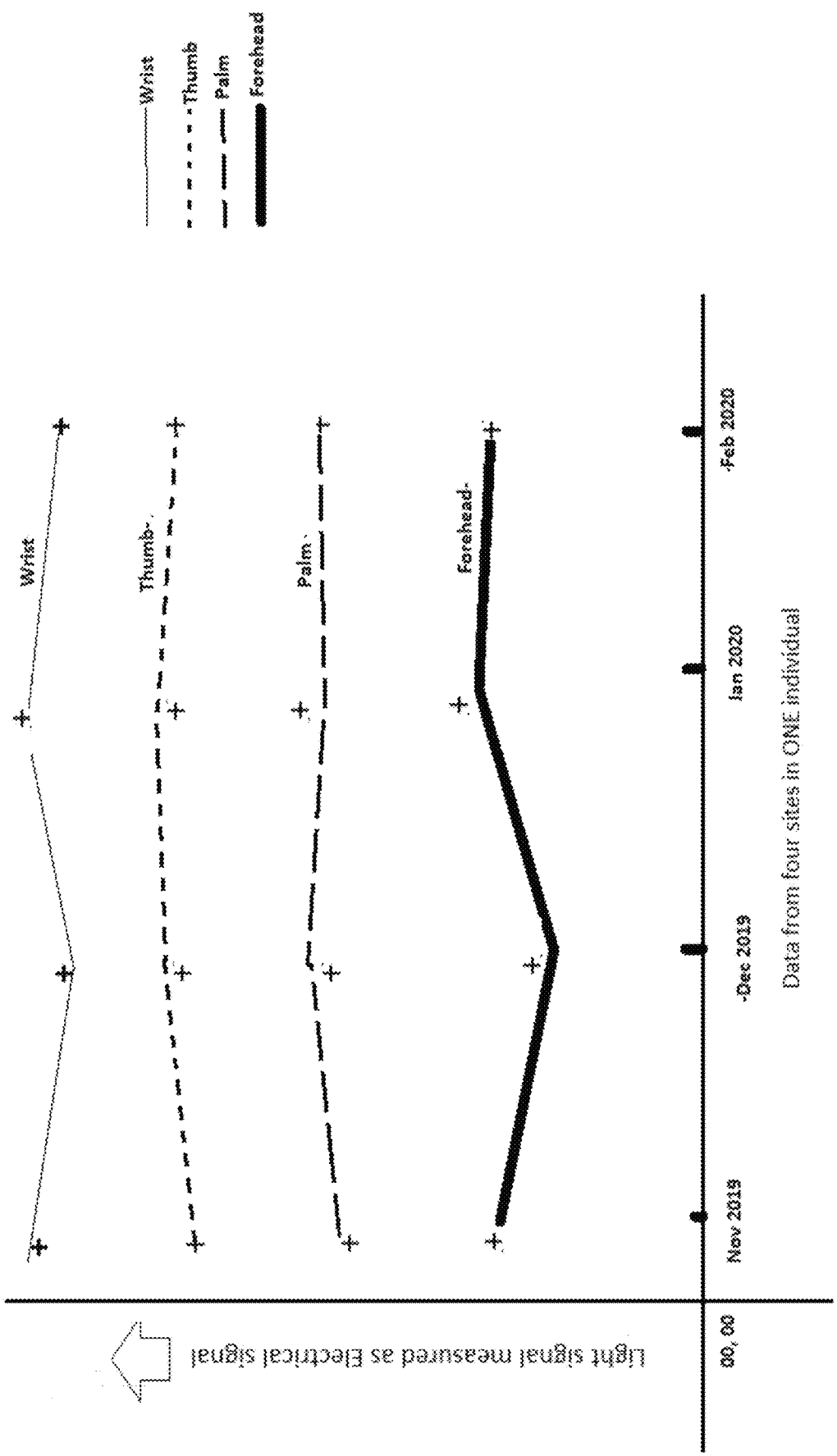
FIG. 9 is a graph of light signal measurements over four different time points for four different areas of a human mammal's skin surface in the same mammal.

In another example, FIG. 9 is the graphical representation of the temporal and spatial data from one individual, using the probe 2 on four different sites at four different time points, each of which were about four weeks apart. The data points, shown as crosses, are the result of a blood draw and laboratory determination of hemoglobin (substantially constant at 14.4 g/dL).

The amount of reflection of light measured as an electrical signal (current) by the one or more sensors 24 is plotted on the Y-axis and the corresponding time point is plotted on the X-axis. As seen from the graph, the readings are substantially reproducible temporally across 4 different timepoints for the same site. However, there is significant difference across readings obtained from different sites. For example, the amount of reflected light from the wrist is higher and it progressively decreases from wrist-thumb-palm-forehead. Therefore, each probe 2 can be designed for a specific reading location, or the probe 2 and processor 4 can be adjusted to account for the different reading location.

Figure 10:
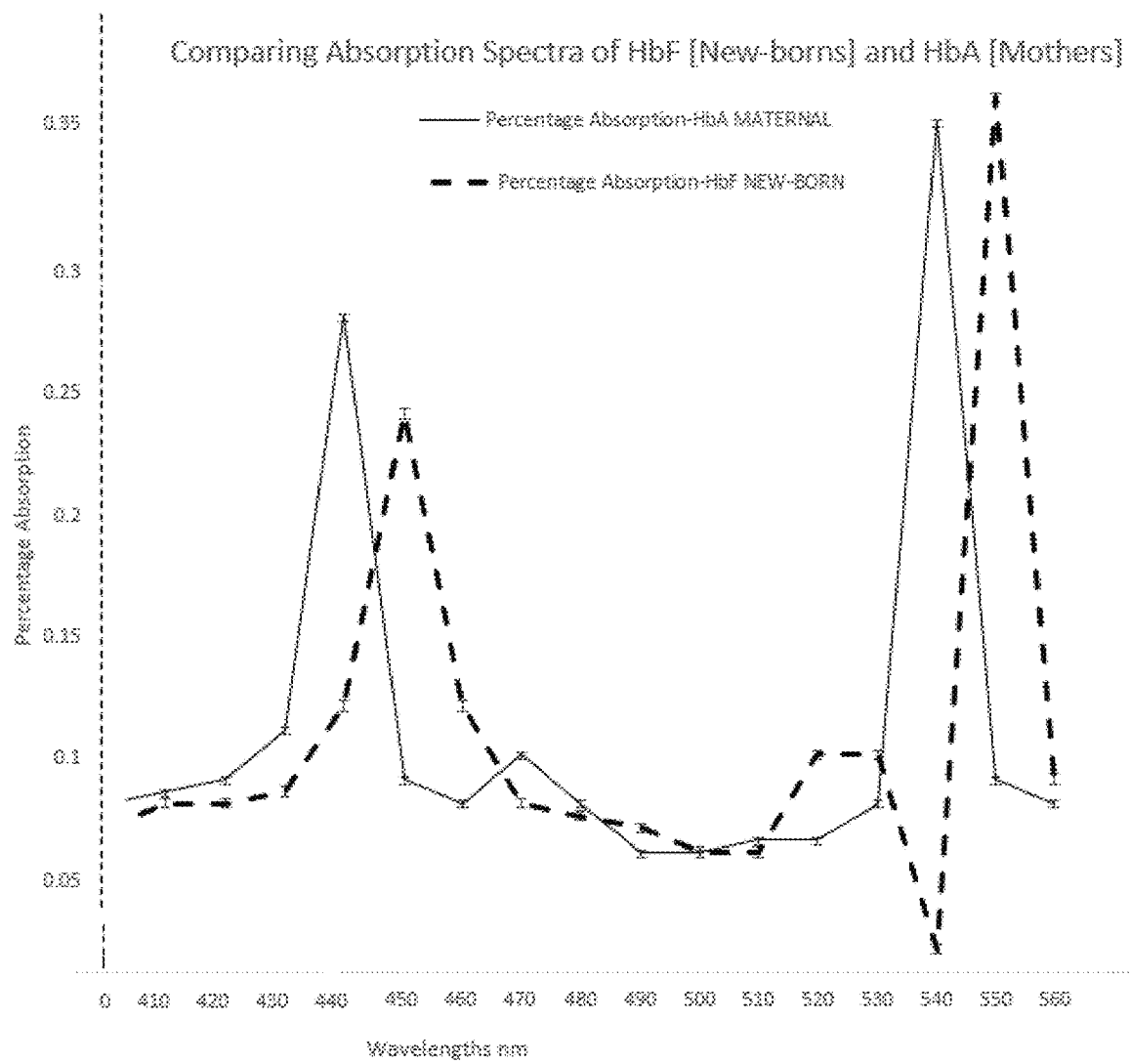
FIG. 10 is a graph of absorption percentage over varying wavelengths for two types of hemoglobin: fetal hemoglobin (Hb-F) and adult hemoglobin (Hb-A).

FIG. 10 is the graphical representation of data from 25 mother-infant pairs, to demonstrate similar spectroscopic properties of fetal hemoglobin (Hb-F) and adult hemoglobin (Hb-A), using the disclosed device. Hb-F is the predominant form of the hemoglobin in newborns and is gradually replaced by Hb-A by 8-9 months of age. The percentage of absorbed light is plotted on the Y-axis and the corresponding wavelength (in nanometers) is plotted on the X-axis. Hb-F and Hb-A have remarkably similar spectroscopic properties with the absorption peaks at 450-460 nm and 540-550 nm. Due to similar spectroscopic properties of blood hemoglobin-A and hemoglobin-F, the disclosed device can be used to measure hemoglobin concentration in adults and infants that are younger than 9 months.

Figure 11:
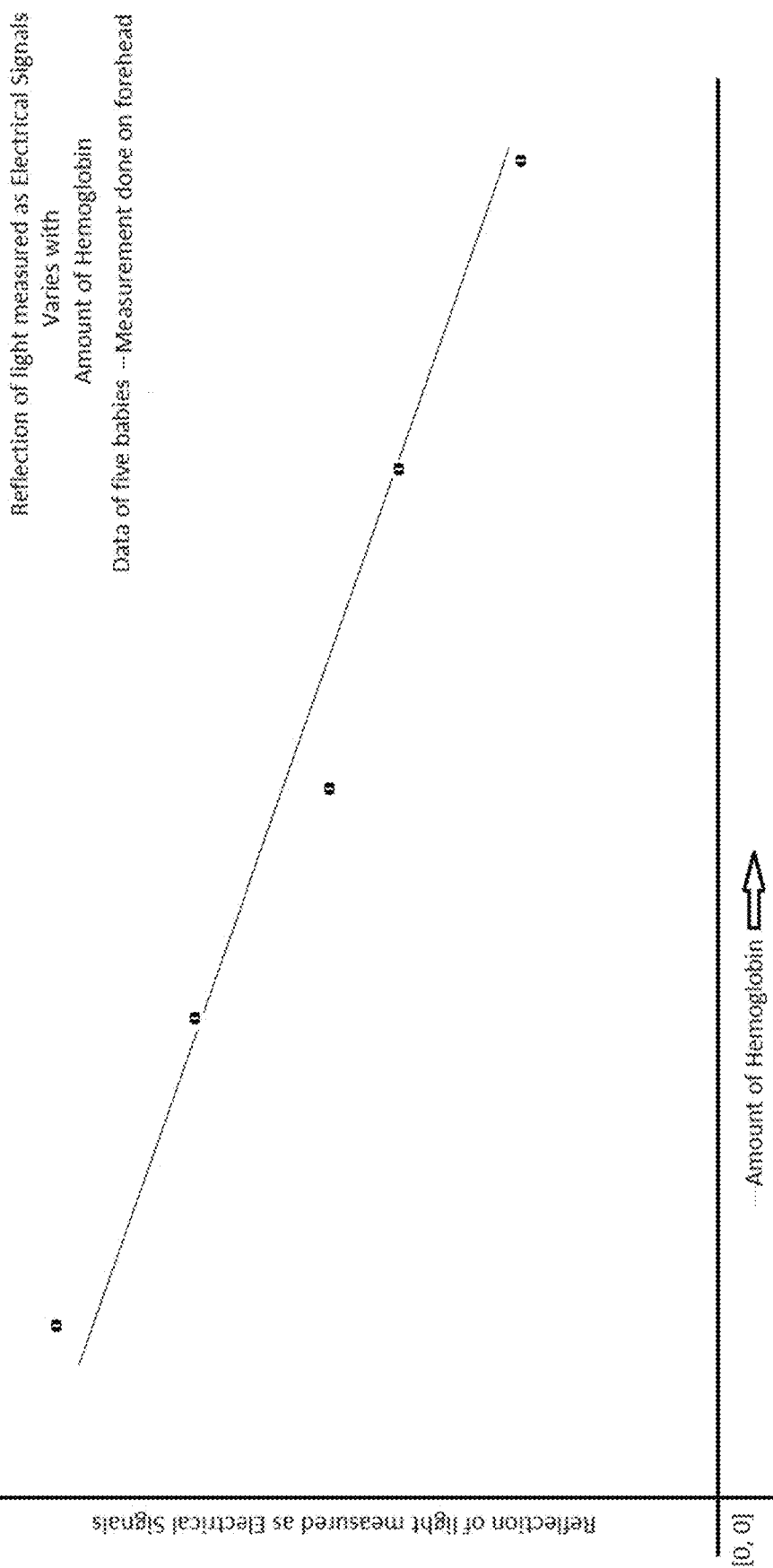
FIG. 11 is a graph of the reflection of light level as compared to hemoglobin level.

As a further demonstration of this, FIG. 11 is the graphical representation of data from 5 infants, with similar melanin content (as measured on the VLS scale), using the probe 2 on the same site for each infant (forehead). The amount of reflection of light measured as an electrical signal (current) by the one or more sensors 24 is plotted on the Y-axis and amount of hemoglobin in the blood is plotted on the X-axis. The five data points indicated by small circles are the laboratory results of a typical blood draw hemoglobin test. The relationship is substantially linear as shown by the substantially straight line, with the laboratory data being near the linear measurement results of the disclosed device.

Further, Table 2 below includes data from four human subjects, with light brown skin color (VLS scale 24-25). Corresponding R values are calculated using the formula, R=E*H. This E was obtained using the disclosed device, and the blood hemoglobin concentration (H) was obtained using the conventional blood draw method. In Table 2, as well as the rest of the disclosure, the "Ratio" of E1 or E2 is the ratio of light emitted by the plurality of LEDs 22 at that wavelength as compared to the amount detected by the at least one sensor 24 at that wavelength.

TABLE 2

| Subject no. | Ratio E1 (525 nm) | Ratio E2 (545 nm) | Total Ratio E = E1 + E2 | Hb (H) measured by blood draw (grams/100 ml) | R value = E * H |
|---|---|---|---|---|---|
| 1 | 0.692 | 0.671 | 1.363 | 13.71 | 18.69 |
| 2 | 0.736 | 0.749 | 1.485 | 12.29 | 18.25 |
| 3 | 0.633 | 0.616 | 1.249 | 14.56 | 18.19 |
| 4 | 0.650 | 0.626 | 1.276 | 14.32 | 18.27 |

E1 = Ratio of reflected light using the 525 nm LED of the disclosed device
E2 = Ratio of reflected light using the 545 nm LED of the disclosed device In Table 2 above and throughout the disclosure, the constant 'R' is related to the hemoglobin but also to the skin color or skin pigment melanin. The constant R would be a function of the amount of skin melanin and/or hemoglobin in the given subset of race/ethnicity. Therefore, this factor "R" would be different across different races/ethnicities.

R can be further depicted as, R=kM Where 'M' represents variable concentration of Melanin in the skin and 'k' is the constant factor related to the hemoglobin.

Due to two variables E (either 1 or 2) and M, the nature of the mathematical relationship between E and H could be substantially linear or substantially logarithmic, and the relationship could be depicted using a substantially logarithmic scale (FIG. 7 noted above) as: R=log (E*H)

The value of R (since R=kM) is dependent on the amount of melanin "M" in the skin. If the value of M is kept substantially constant, the value of R would be substantially constant. In other words, the value of R will be substantially constant for the subjects with the same skin melanin concentration (M). In such case, the relationship would tend to be substantially linear, and can be expressed (FIG. 6) as: R=E*H Because the disclosed device measures E at various wavelengths, the amount of hemoglobin H (in grams/100 ml) in the blood can be calculated by the processor 4, with the formula: H (in grams/100 ml)=R/E The value of R can be obtained through a melanin concentration determination. As noted above, the value of R is variable depending on the skin melanin concentration and would be constant for a specific melanin concentration. Subjects with lighter skin color (with less melanin, such as Caucasian human subjects) have higher R values, compared to the subjects with the darker skin color (with more melanin, such as African American human subjects), with R being substantially constant for subjects with the same or similar melanin concentrations.

The mean and the standard deviation of the R values obtained in Table 2 were calculated. The mean calculated R value, with the standard deviation (S.D), in this case is (mean=18.35, S.D=0.23). Using a 95% confidence interval (CI) for the data of Table 2 case would be: Mean+/−2 S.D for 95% CI is (17.89-18.81). Therefore, the R value for human subjects with the light skin tone (VLS 24-25) is expected to be around 18.35 and would fall between the intervals of 17.89 to 18.81 for at least 95% of the subjects measured.

Similarly, to Table 2 above, Table 3 below is a representation of data from three human subjects, with dark brown skin color (VLS scale 30-31). Corresponding R values were calculated using the formula, R=E*H. Although only one time point is listed in Table 3 for each of the subjects, in other examples, multiple measurements can be undertaken for each subject. These multiple measurements can span the time ranges noted above, such as continuous or near continuous measurement, up to a measurement every several minutes or more.

TABLE 3

| Subject no | Ratio 1 (525 nm) | Ratio 2 (545 nm) | Total Ratio E = E1 + E2 | Hb (H) measured by blood draw. (grams/100 ml) | R value = E * H |
|---|---|---|---|---|---|
| 1 | 0.360 | 0.368 | 0.728 | 15.71 | 11.43 |
| 2 | 0.396 | 0.395 | 0.791 | 14.60 | 11.55 |
| 3 | 0.382 | 0.367 | 0.749 | 16.30 | 12.21 |

E1 = Ratio of reflected light using the 525 nm LED of the disclosed device
E2 = Ratio of reflected light using the 545 nm LED of the disclosed device Similarly, to the procedure in Table 2, discussed above, for the data of Table 3, the calculated mean and S.D was (mean=11.73, S.D=0.42). Thus, using a 95% confidence interval (CI) for Table 3, Mean+/−2 S.D for 95% CI is (10.89-12.57). Therefore, the R value for subjects with the dark skin tone (VLS scale 30-31) is expected to be around 11.73 and would fall between the intervals of 10.89 to 12.57 for at least 95% of the subjects measured.

Table 4 is a representation of data from two human subjects. Subject X with light brown skin color (VLS grade 24) and subject Y with dark brown skin color (VLS grade 30).

TABLE 4

| Subject | Skin color | Ratio E1 (525 nm) | Ratio E2 (550 nm) | Total Ratio E = E1 + E2 | R value for each skin color obtained from previous experiments with (95% C.I.) | Total hemoglobin (H, (grams/100 ml) calculated by the device using H = R/E with (95% C.I.) | Hemoglobin measured using blood draw. (grams/100 ml) | Difference (grams/100 ml)% |
|---|---|---|---|---|---|---|---|---|
| X | Light | 0.668 | 0.672 | 1.340 | 18.35 (17.89-18.81) | 13.69 (13.35-14.0) | 13.90 | (−0.21, 1.5) |
| Y | Dark | 0.411 | 0.396 | 0.807 | 11.73 (10.89-12.57) | 14.53 (13.49-15.58) | 14.80 | (−0.27, 1.82) |

E1 = Ratio of reflected light using the 525 nm LED of the disclosed device.
E2 = Ratio of reflected light using the 545 nm LED of the disclosed device.
95% C.I. = 95% confidence interval obtained by Mean ± 2 (Standard deviation).

In Table 4, for each subject, values of E were obtained using the disclosed device (column 4). Next, depending upon the skin color, corresponding mean R values (with 95% C.I.) for each skin color were chosen as shown in column 5 (based on Tables 2 and 3 above). Hemoglobin values were calculated using the formula, H=R/E, and are shown in column 6 along with the limits of agreement. These values were compared to those obtained by the conventional blood draw method (column 7).

As shown in column 8, the differences between the hemoglobin values obtained using the disclosed device and conventional blood draw are remarkably small and fall well within the limits of agreement. Specifically, for both subject X and subject Y, the disclosed device was able to accurately estimate the blood hemoglobin value. The calculated values 13.69 (grams/100 ml) (for Subject X) and 14.53 (grams/100 ml) (for Subject Y) are close to the values measured by the conventional blood draw method (13.90 (grams/100 ml) and 14.8 (grams/100 ml) respectively. In both examples, the difference between the device calculated hemoglobin value and the traditional (blood) draw measured value was about 0.2-0.3 (grams/100 ml). This difference is small and is significantly less than the currently available, approved by the Food and Drug Administration (FDA), non-invasive devices.

As a further example, multiple readings were obtained from a number of subjects with different skin colors using the disclosed device on the back of each of their wrists. The R value and mean were calculated for each individual relied on for data in Tables 2 and 3.

Figure 12:
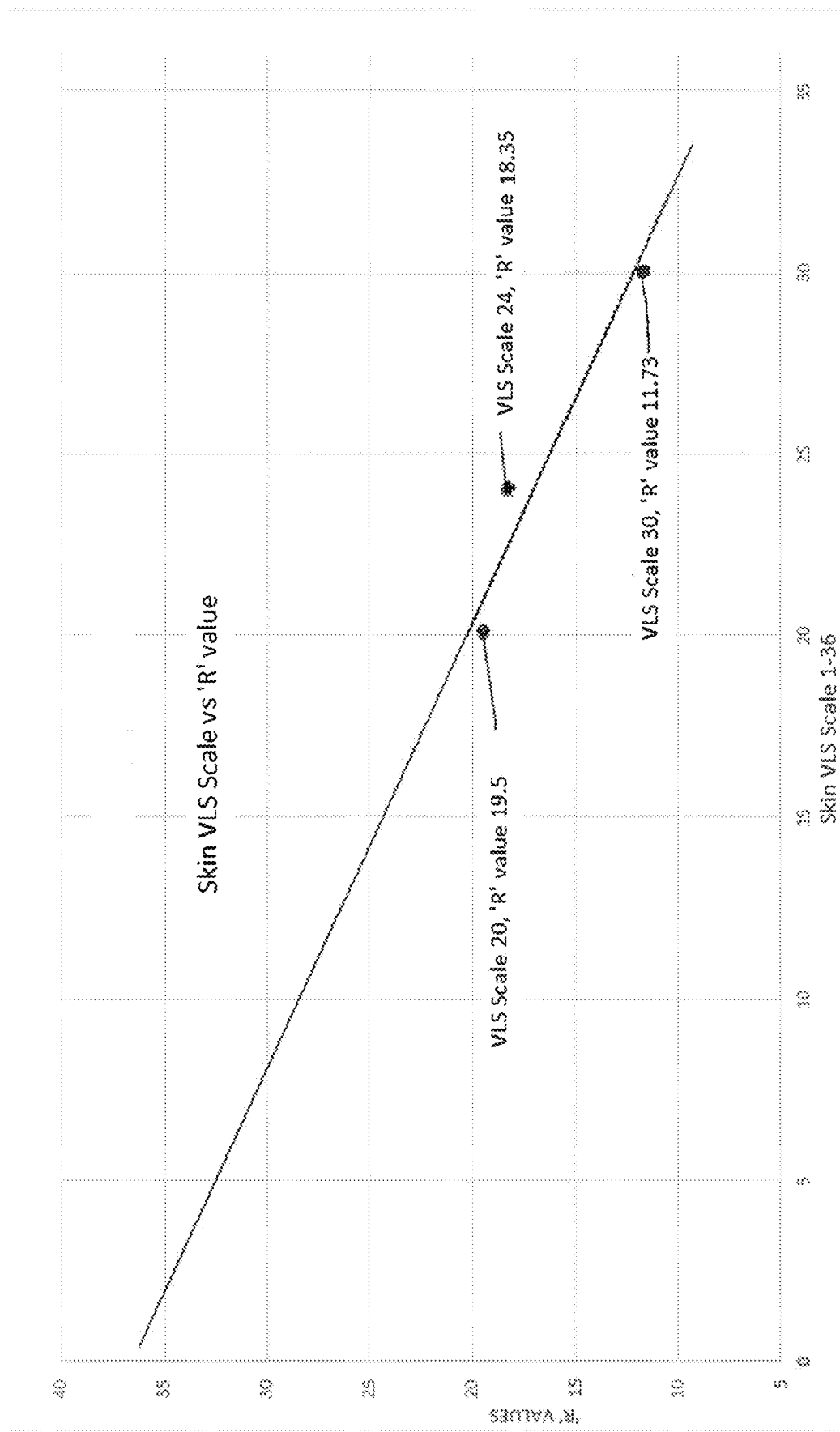
FIG. 12 is a graph of the R value as compared to various skin colors.

The average R was then plotted on the Y-axis and corresponding skin color (categorical VLS scale from 1-36) on the X-axis. These results are illustrated in FIG. 12. For subjects with light skin color (VLS 20), the mean R value was 19.5. For subjects with slightly darker skin (VLS 24), the mean R value was 18.35. The R value further decreases (mean value 11.73) for subjects with very dark skin (VLS 30). This data demonstrates a relatively consistent, substantially linear inverse relationship between the VLS scales and the R value. These findings support that the R value is significantly lower (around 5-10) in subjects with higher VLS scales as compared (around 35-40) to subjects with lower VLS scales.

Example 1

In this example, a patient enters a clinical setting. The operator then places the probe 2 on a portion of the patient, for example the patient's wrist.

The one or more sensors 24 detect reflected light, in this example at 525 nm and 545 nm, such that the processor 4 can determine the ratio of both of E1 and E2. The processor 4 makes this determination by determining the ratio of returned light detected by the one or more sensors in comparison to the emitted light from the plurality of LEDs 22, at each wavelength.

The processor 4 then outputs two ratios (E1) and (E2). The processor 4 can then add those values (E1)+(E2) (or a user can manually add those ratios) to determine a total E value. Next, the VLS scale value is determined in one of two ways.

The first way is for a user to estimate the value by a visual inspection and assignment of the patient to a score of 1-36 on the VLS scale. Under this first option, the operator can then manually select the corresponding R value for the selected score (present on a provided chart that includes all VLS scale scores and their corresponding R values). The operator can then manually divide the R value by E.

The second way is for the probe 2 to include an optical sensor (one or more sensors 24, or an additional sensor) that can receive a signal, and the processor 4 can, based on the signal, automatically assign the patient to a VLS scale value (with its corresponding R value), with those VLS scale values and R values being stored in the electronic storage device 10. The processor 4 can then divide the R value by the obtained E value to determine the total hemoglobin value.

Example 2

In addition to the total hemoglobin as described above in Example 1, the disclosed device can also measure the ratio of oxy-hemoglobin (O-Hb) to deoxy-hemoglobin (d-Hb), as well as change in the ratio, as discussed in this example.

In this example, a patient enters a clinical setting. The operator then places the probe 2 on a portion of the patient, for example the patient's wrists. The total hemoglobin value is then obtained as discussed in Example 1.

Further, since E1 substantially corresponds to the data collected at the 525 nm wavelength, it is indicative of oxy-hemoglobin concentration, while E2, substantially corresponding to data collected at the 550 nm level (in this example, however, about 545 nm level can also be used for data collection), is indicative of deoxy-hemoglobin concentration. The ratio of E1 to E2 can be determined once, or sequentially to monitor the patient's condition.

In this example, blood hemoglobin was measured with the disclosed device for a patient presenting an acute asthma attack. Asthma causes airways to become inflamed and constrict, leading to low oxygen concentration in the blood. The patient had a VLS skin scale of 20, with the corresponding R value of 19.5 based on a value demonstrated by FIG. 12.

At first, the patient had symptoms of breathlessness and cough. The obtained readings are depicted immediately after presentation, at time 2 minutes (Table 5), with the disclosed device. Patient was then observed and treated with medications to relieve cough and breathlessness. However, patient's clinical condition deteriorated. Another set of readings is obtained at 21 minutes with the disclosed device. Patient was subsequently treated with a supplemental oxygen face mask. Patient's condition improved, and a repeat set of observations were obtained after about 20 minutes of oxygen therapy (at 40 minutes), with the disclosed device.

TABLE 5

| Time (mins) | Ratio E1 (525 nm) | Ratio E2 (550 nm) | Ratio E1/E2 | Total ratio E (E1 + E2) | R value for skin VLS 20 | Calculated Hb using the device, H = R/E (grams/100 ml) | Measured Hb using the blood draw method. (grams/100 ml) | Oxygen saturation using arterial blood gas (normal 97-100%) |
|---|---|---|---|---|---|---|---|---|
| 2 min (room air) | 0.631 | 0.608 | 1.038 | 1.239 | 19.50 | 15.74 | 15.30 | 90% |
| 21 min (room air) | 0.652 | 0.588 | 1.109 | 1.240 | 19.50 | 15.73 | 15.40 | 86% |
| 40 min (Oxygen face mask) | 0.615 | 0.622 | 0.988 | 1.237 | 19.50 | 15.76 | 15.30 | 96% |

E1 = Ratio of reflected light using the 525 nm LED of the disclosed device
E2 = Ratio of reflected light using the 545 nm LED of the disclosed device The E1 divided by E2 ratio was obtained at each time point by the processor 4. As seen from Table 5, the ratio increased from 1.038 to 1.109 as patient's clinical condition worsened. After treatment with the supplemental oxygen, patient's condition improved, and the E1/E2 ratio decreased to 0.988. These results are shown in the FIG. 13.

Specifically, in FIG. 13, the ratio of E1/E2 measured using the disclosed device, is plotted on the Y axis, and the corresponding time point (in minutes) is plotted on the X axis. At presentation, the patient had hypoxia (low oxygen content), with E1/E2 ratio 1.038. After 20 minutes, patient's condition and hypoxia worsened, with corresponding increase the ratio to 1.109. Patient was subsequently treated using supplemental oxygen. Patient's hypoxia improved, correlated with the ratio of 0.988.

As seen in FIG. 13, as the ratio of E1/E2 increases, the blood oxygen saturation (an indicator of oxyhemoglobin) decreases. Since E and H have an inverse relationship as previously described (FIG. 6), the ratio E1/E2 is expected to have an inverse relationship with the relative oxy-hemoglobin (O-Hb) concentration. Oxy-hemoglobin is the form of hemoglobin attached to the oxygen molecules and is responsible for the oxygen delivery to the tissue.

Therefore, ratio E1/E2 provides a tool to monitor patient's clinical condition without requiring the need for the invasive arterial blood gas sampling. The ratio can be calculated at the bedside by a user, or the processor 4 could determine this ratio. Currently available non-invasive method (pulse-oximetry) to measure blood oxygen saturation, has limitations in dark-skinned subjects, and during low perfusion states, such as shock. The disclosed device does not have these limitations.

Since the relative ratios of oxy and deoxy hemoglobin are unique for each individual, the absolute value of ratio E1/E2 would vary between individuals. However, the ratio E1/E2 would be specific for the given subject and could be used through serial measurements as a non-invasive means of oxyhemoglobin monitoring. This can significantly decrease the need for the invasive blood collection.

The described embodiments and examples of the present disclosure are intended to be illustrative rather than restrictive and are not intended to represent every embodiment or example of the present disclosure. While the fundamental novel features of the disclosure as applied to various specific embodiments thereof have been shown, described, and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

The invention claimed is:

1. A device comprising:
   a plurality of light emitting diodes configured to emit light at a wavelength in a range of about 515 nm to about 535 nm and emit light at a wavelength in a range of about 535 nm to about 555 nm towards a surface of a mammal's skin surface;
   one or more sensors configured to detect an amount of reflected light in a range of about 515 nm to about 535 nm and a range of about 535 nm to about 555 nm, wherein the detected, reflected light is the emitted light that passes through at least a portion of the mammal's skin and is at least partially reflected towards the one or more sensors, wherein the one or more sensors are configured to output a signal comprising both the amount of the detected, reflected light in the range of about 515 nm to about 535 nm and the amount of the detected, reflected light in the range of about 535 nm to about 555 nm; and
   a processor configured to:
      send a signal of emitted light at the wavelength in the range of about 515 nm to about 535 nm and a signal of emitted light at the wavelength in the range of about 535 nm to about 555 nm,
      receive the signal of the amount of the detected, reflected light in the range of about 515 nm to about 535 nm and the range of about 535 nm to about 555 nm and the signal of the amount of the detected, reflected light in the range of about 535 nm to about 555 nm,
      determine a first ratio of reflected light, wherein the first ratio is a percentage of detected, reflected light in the range of about 515 nm to about 535 nm as compared to the light emitted in the range of about 515 nm to about 535 nm,
      determine a second ratio of reflected light, wherein the second ratio is a percentage of detected, reflected light in the range of about 535 nm to about 555 nm as compared to the light emitted in the range of about 535 nm to about 555 nm,
      determine a total ratio by adding the first ratio to the second ratio, and
      determine a total hemoglobin value by dividing a melanin content R value by the total ratio; and
      output values of the total ratio and the total hemoglobin value.

2. The device of claim 1, wherein
   the first ratio is the percentage of light emitted in the range of about 520 nm to about 530 nm as compared to the light reflected in the range of about 520 nm to about 530 nm: and
   the second ratio is the percentage of light emitted in the range of about 540 nm to about 550 nm as compared to the light reflected in the range of about 540 nm to about 550 nm.

3. The device of claim 1, wherein
   the first ratio is the percentage of light emitted in the range of about 525 as compared to the light reflected in the range of about 525; and
   the second ratio is the percentage of light emitted in the range of about 545 nm as compared to the light reflected in the range of about 545.

4. The device of claim 1, wherein the values of the total ratio and the total hemoglobin value are output to a display that is configured to display text and/or images of the values.

5. The device of claim 4, wherein the display is configured to receive a touch input.

6. The device of claim 1, wherein the melanin content R value is based on a correlation of Felix Von Luschan (VLS) skin color scale value to the melanin content R value.

7. The device of claim 6, wherein the VLS skin color scale value is determined by a visual inspection by an operator.

8. The device of claim 6, wherein the device further comprises an optical sensor configured to detect a color signal of the mammal's skin surface, and wherein the processor is configured to automatically assign the mammal the melanin content R value based on the color signal.

9. The device of claim 6, further comprising an electronic storage device configured to store VLS skin color scale values and their associated melanin content R values.

10. The device of claim 1, wherein the processor is further configured to output a ratio of oxy-hemoglobin to deoxy-hemoglobin (E1/E2 ratio).

11. A method of determining a hemoglobin level of a mammal, the method comprising:
   contacting the mammal's skin with a device, the device comprising:
      a plurality of light emitting diodes configured to emit light at a wavelength in a range of about 515 nm to about 535 nm and emit light at a wavelength in a range of about 535 nm to about 555 nm towards a surface of a mammal's skin surface;
      one or more sensors configured to detect an amount of reflected light in a range of about 515 nm to about 535 nm and a range of about 535 nm to about 555 nm, wherein the detected, reflected light is the emitted light that passes through at least a portion of the mammal's skin and is at least partially reflected towards the one or more sensors, wherein the one or more sensors are configured to output a signal comprising both the amount of the detected, reflected light in the range of about 515 nm to about 535 nm and the amount of the detected, reflected light in the range of about 535 nm to about 555 nm; and
      a processor configured to:
         send a signal of emitted light at the wavelength in the range of about 515 nm to about 535 nm and a signal of emitted light at the wavelength in the range of about 535 nm to about 555 nm, receive the signal of the amount of the detected, reflected light in the range of about 515 nm to about 535 nm and the range of about 535 nm to about 555 nm and the signal of the amount of the detected, reflected light in the range of about 535 nm to about 555 nm, determine a first ratio of reflected light, wherein the first ratio is a percentage of detected, reflected light in the range of about 515 nm to about 535 nm as compared to the light emitted in the range of about 515 nm to about 535 nm, determine a second ratio of reflected light, wherein the second ratio is a percentage of detected, reflected light in the range of about 535 nm to about 555 nm as compared to the light emitted in the range of about 535 nm to about 555 nm, determine a total ratio by adding the first ratio to the second ratio, and determine a total hemoglobin value by dividing a melanin content R value by the total ratio; and outputting the total hemoglobin.

12. The method of claim 11, wherein the outputting is received by a display that is configured to display text and/or images of the values of the total ratio and the total hemoglobin value.

13. The method of claim 12, wherein the display is configured to receive a touch input.

14. The method of claim 11, wherein the melanin content R value is based on a correlation of Felix Von Luschan (VLS) skin color scale value to the melanin content R value.

15. The method of claim 11, wherein the processor is further configured to determine a ratio of oxy-hemoglobin to deoxy-hemoglobin (E1/E2 ratio), and the method further comprises outputting the ratio of oxy-hemoglobin to deoxy-hemoglobin (E1/E2 ratio).

* * * * *